US012584915B2

(12) United States Patent
Rizk et al.

(10) Patent No.: US 12,584,915 B2
(45) Date of Patent: Mar. 24, 2026

(54) GLYPHOSATE BIOSENSOR

(71) Applicant: THE TRUSTEES OF INDIANA UNIVERSITY, Bloomington, IN (US)

(72) Inventors: Shahir S. Rizk, South Bend, IN (US); Maggie M. Fink, South Bend, IN (US); Pierre Emmanuel Yoann N'Guetta, Carrboro, NC (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 1103 days.

(21) Appl. No.: 17/628,056

(22) PCT Filed: Aug. 3, 2020

(86) PCT No.: PCT/US2020/044697
§ 371 (c)(1),
(2) Date: Jan. 18, 2022

(87) PCT Pub. No.: WO2021/022245
PCT Pub. Date: Feb. 4, 2021

(65) Prior Publication Data
US 2022/0276241 A1    Sep. 1, 2022

Related U.S. Application Data

(60) Provisional application No. 62/881,393, filed on Aug. 1, 2019.

(51) Int. Cl.
C07K 19/00          (2006.01)
C07K 14/245        (2006.01)
G01N 33/557        (2006.01)

(52) U.S. Cl.
CPC ......... *G01N 33/557* (2013.01); *C07K 14/245* (2013.01); *C07K 19/00* (2013.01)

(58) Field of Classification Search
None
See application file for complete search history.

(56) References Cited

U.S. PATENT DOCUMENTS

2004/0118681 A1    6/2004  Hellinga et al.

FOREIGN PATENT DOCUMENTS

| EP | 3508575 A1 | 7/2019 |
| WO | 2013052946 A2 | 4/2013 |

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) the Protein Folding Problem and Tertiary Structure Prediction. Birkhauser: Boston, pp. 491-495.*

Skolnick et al. (2000). Trends in Biotech. 18(1):34-39.*

PCT International Search Report and Written Opinion completed by the ISA/US on Oct. 15, 2020 and issued in connection with PCT/US2020/044697.

Rizk, Shahir S et al. "Identification of cognate ligands for the *Escherichia coli* phnD protein product and engineering of a reagentless fluorescent biosensor for phosphonates." Protein science : a publication of the Protein Society vol. 15,7 (2006): 1745-51. doi:10.1110/ps.062135206.

Alicea, Ismael et al. "Structure of the *Escherichia coli* phosphonate binding protein PhnD and rationally optimized phosphonate biosensors." Journal of molecular biology vol. 414,3 (2011): 356-69. doi:10.1016/j.jmb.2011.09.047 and "Supplementary data", Oct. 12, 2011, retrieved from the internet: URL: https://www.ncbi.nlm.nih.gov/pmc/articles/PMC5320564/bin/NIHMS344923-supplement-01.pdf.

N'Guetta, Pierre-Emmanuel Y et al. "Engineering a fluorescence biosensor for the herbicide glyphosate." Protein engineering, design & selection : PEDS vol. 33 (2020): gzaa021. doi:10.1093/protein/gzaa021.

Supplementary European Search Report for EP20846378, mailed Jul. 4, 2023.

* cited by examiner

Primary Examiner — Christine J Saoud
Assistant Examiner — Jon M Lockard
(74) Attorney, Agent, or Firm — Barnes & Thornburg LLP

(57) ABSTRACT

Disclosed herein are engineered proteins for the detection of glyphosate in soil, water, and the like without the need for additional reagents.

10 Claims, 6 Drawing Sheets

Specification includes a Sequence Listing.

2-AEP                    Glyphosate

SEQUENCE LISTING

<160> NUMBER OF SEQ ID NOS: 17

<210> SEQ ID NO 1
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Glu Glu Gln Glu Lys Ala Leu Asn Phe Gly Ile Ile Ser Thr Glu Ser
1               5                   10                  15

Gln Gln Asn Leu Lys Pro Gln Trp Thr Pro Phe Leu Gln Asp Met Glu
            20                  25                  30

Lys Lys Leu Gly Val Lys Val Asn Ala Phe Phe Ala Pro Asp Tyr Ala
        35                  40                  45

Gly Ile Ile Gln Gly Met Arg Phe Asn Lys Val Asp Ile Ala Trp Tyr
    50                  55                  60

Gly Asn Leu Ser Ala Met Glu Ala Val Asp Arg Ala Asn Gly Gln Val
65                  70                  75                  80

Phe Ala Gln Thr Val Ala Ala Asp Gly Ser Pro Gly Tyr Trp Ser Val
                85                  90                  95

Leu Ile Val Asn Lys Asp Ser Pro Ile Asn Asn Leu Asn Asp Leu Leu
            100                 105                 110

Ala Lys Arg Lys Asp Leu Thr Phe Gly Asn Gly Asp Pro Cys Ser Thr
        115                 120                 125

Ser Gly Phe Leu Val Pro Gly Tyr Tyr Val Phe Ala Lys Asn Asn Ile
```

-continued

```
          130              135                140

Ser Ala Ser Asp Phe Lys Arg Thr Val Asn Ala Gly His Glu Thr Asn
145                 150                155                160

Ala Leu Ala Val Ala Asn Lys Gln Val Asp Val Ala Thr Asn Asn Thr
                165                170                175

Asn Asn Leu Asp Lys Leu Lys Thr Ser Ala Pro Glu Lys Leu Lys Glu
            180                185                190

Leu Lys Val Ile Trp Lys Ser Pro Leu Ile Pro Gly Asp Pro Ile Val
            195                200                205

Trp Arg Lys Asn Leu Ser Glu Thr Thr Lys Asp Lys Ile Tyr Asp Phe
        210                215                220

Phe Met Asn Tyr Gly Lys Thr Pro Glu Glu Lys Ala Val Leu Glu Arg
225                 230                235                240

Leu Gly Trp Ala Pro Phe Arg Ala Ser Ser Asp Leu Gln Leu Val Pro
                245                250                255

Ile Arg Gln Leu Ala Leu Phe Lys Glu Met Gln Gly Val Lys Ser Asn
                260                265                270

Lys Gly Leu Asn Glu Gln Asp Lys Leu Ala Lys Thr Thr Glu Ile Gln
            275                280                285

Ala Gln Leu Asp Asp Leu Asp Arg Leu Asn Asn Ala Leu Ser Ala Met
        290                295                300

Ser Ser Val Ser Lys Ala Val Gln
305                 310
```

```
<210> SEQ ID NO 2
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Glu Gln Glu Lys Ala Leu Asn Phe Gly Ile Ile Ser Thr Glu Ser
1               5                  10                 15

Gln Gln Asn Leu Lys Pro Gln Trp Thr Pro Phe Leu Gln Asp Met Glu
            20                 25                 30

Lys Lys Leu Gly Val Lys Val Asn Ala Phe Phe Ala Pro Asp Tyr Ala
        35                 40                 45

Gly Ile Ile Gln Gly Met Arg Phe Asn Lys Val Asp Ile Ala Trp Tyr
    50                 55                 60

Gly Asn Leu Ser Ala Met Glu Ala Val Asp Arg Ala Asn Gly Gln Val
65                 70                 75                 80

Phe Ala Gln Thr Val Ala Ala Asp Gly Ser Pro Gly Tyr Trp Ser Val
                85                 90                 95

Leu Ile Val Asn Lys Asp Ser Pro Ile Asn Asn Leu Asn Asp Leu Leu
                100                105                110

Ala Lys Arg Lys Asp Leu Thr Phe Gly Asn Gly Asp Pro Cys Ser Thr
            115                120                125

Ser Gly Phe Leu Val Pro Gly Tyr Tyr Val Phe Ala Lys Asn Asn Ile
            130                135                140

Ser Ala Ser Asp Phe Lys Arg Thr Val Asn Ala Gly His Glu Thr Asn
145                 150                155                160

Ala Leu Ala Val Ala Asn Lys Gln Val Asp Val Ala Thr Asn Asn Thr
                165                170                175
```

```
Asn Asn Leu Asp Lys Leu Lys Thr Ser Ala Pro Glu Lys Leu Lys Glu
            180                 185                 190

Leu Lys Val Ile Trp Lys Ser Pro Leu Ile Pro Gly Ser Pro Ile Val
            195                 200                 205

Trp Arg Lys Asn Leu Ser Glu Thr Thr Lys Asp Lys Ile Tyr Asp Phe
        210                 215                 220

Phe Met Asn Tyr Gly Lys Thr Pro Glu Glu Lys Ala Val Leu Glu Arg
225                 230                 235                 240

Leu Gly Trp Ala Pro Phe Arg Ala Ser Ser Asp Leu Gln Leu Val Pro
                245                 250                 255

Ile Arg Gln Leu Ala Leu Phe Lys Glu Met Gln Gly Val Lys Ser Asn
            260                 265                 270

Lys Gly Leu Asn Glu Gln Asp Lys Leu Ala Lys Thr Thr Glu Ile Gln
        275                 280                 285

Ala Gln Leu Asp Asp Leu Asp Arg Leu Asn Asn Ala Leu Ser Ala
    290                 295                 300

<210> SEQ ID NO 3
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Glu Gln Glu Lys Ala Leu Asn Phe Gly Ile Ile Ser Thr Glu Ser
1               5                   10                  15

Gln Gln Asn Leu Lys Pro Gln Trp Thr Pro Phe Leu Gln Asp Met Glu
            20                  25                  30

Lys Lys Leu Gly Val Lys Val Asn Ala Phe Phe Ala Pro Asp Tyr Ala
            35                  40                  45

Gly Ile Ile Gln Gly Met Arg Phe Asn Lys Val Asp Ile Ala Trp Tyr
        50                  55                  60

Gly Asn Leu Ser Ala Met Glu Ala Val Asp Arg Ala Asn Gly Gln Val
65                  70                  75                  80

Phe Ala Gln Thr Val Ala Ala Asp Gly Ser Pro Gly Tyr Trp Ser Val
                85                  90                  95

Leu Ile Val Asn Lys Asp Ser Pro Ile Asn Asn Leu Asn Asp Leu Leu
            100                 105                 110

Ala Lys Arg Lys Asp Leu Thr Phe Gly Asn Gly Asp Pro Cys Ser Thr
        115                 120                 125

Ser Gly Phe Leu Val Pro Gly Tyr Tyr Val Phe Ala Lys Asn Asn Ile
    130                 135                 140

Ser Ala Ser Asp Phe Lys Arg Thr Val Asn Ala Gly His Glu Thr Asn
145                 150                 155                 160

Ala Leu Ala Val Ala Asn Lys Gln Val Asp Val Ala Thr Asn Asn Thr
                165                 170                 175

Asn Asn Leu Asp Lys Leu Lys Thr Ser Ala Pro Glu Lys Leu Lys Glu
            180                 185                 190

Leu Lys Val Ile Trp Lys Ser Pro Leu Ile Pro Gly Ser Pro Ile Val
            195                 200                 205

Trp Arg Lys Asn Leu Ser Glu Thr Thr Lys Asp Lys Ile Tyr Asp Phe
        210                 215                 220

Phe Met Asn Tyr Gly Lys Thr Pro Glu Glu Lys Ala Val Leu Glu Arg
225                 230                 235                 240
```

```
Leu Gly Trp Ala Pro Phe Arg Ala Ser Ser Asp Leu Gln Leu Val Pro
                245                 250                 255

Ile Arg Gln Leu Ala Leu Phe Lys Glu Met Gln Gly Val Lys Ser Asn
            260                 265                 270

Lys Gly Leu Asn Glu Gln Asp Lys Leu Ala Lys Thr Thr Glu Ile Gln
        275                 280                 285

Ala Gln Leu Asp Asp Leu Asp Arg Leu Asn Asn Ala Leu Ser Ala Met
    290                 295                 300

Ser Ser Val Ser Lys Ala Val Gln
305                 310

<210> SEQ ID NO 4
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Glu Gln Glu Lys Ala Leu Asn Phe Gly Ile Ile Ser Thr Glu Ser
1               5                   10                  15

Gln Gln Asn Leu Lys Pro Gln Trp Thr Pro Phe Leu Gln Asp Met Glu
            20                  25                  30

Lys Lys Leu Gly Val Lys Val Asn Ala Phe Phe Ala Pro Asp Tyr Ala
        35                  40                  45

Gly Ile Ile Gln Gly Met Arg Phe Asn Lys Val Asp Ile Ala Trp Tyr
    50                  55                  60

Gly Asn Leu Ser Ala Met Glu Ala Val Asp Arg Ala Asn Gly Gln Val
65                  70                  75                  80

Phe Ala Gln Thr Val Ala Ala Asp Gly Ser Pro Gly Tyr Trp Ser Val
                85                  90                  95

Leu Ile Val Asn Lys Asp Ser Pro Ile Asn Asn Leu Asn Asp Leu Leu
            100                 105                 110

Ala Lys Arg Lys Asp Leu Thr Phe Gly Asn Gly Asp Pro Cys Ser Thr
        115                 120                 125

Ser Gly Phe Leu Val Pro Gly Tyr Tyr Val Phe Ala Lys Asn Asn Ile
    130                 135                 140

Ser Ala Ser Asp Phe Lys Arg Thr Val Asn Ala Gly His Glu Thr Asn
145                 150                 155                 160

Ala Leu Ala Val Ala Asn Lys Gln Val Asp Val Ala Thr Asn Asn Thr
                165                 170                 175

Glu Asn Leu Asp Lys Leu Lys Thr Ser Ala Pro Glu Lys Leu Lys Glu
            180                 185                 190

Leu Lys Val Ile Trp Lys Ser Pro Leu Ile Pro Gly Asn Pro Ile Val
        195                 200                 205

Trp Arg Lys Asn Leu Ser Glu Thr Thr Lys Asp Lys Ile Tyr Asp Phe
    210                 215                 220

Phe Met Asn Tyr Gly Lys Thr Pro Glu Glu Lys Ala Val Leu Glu Arg
225                 230                 235                 240

Leu Gly Trp Ala Pro Phe Arg Ala Ser Ser Asp Leu Gln Leu Val Pro
                245                 250                 255

Ile Arg Gln Leu Ala Leu Phe Lys Glu Met Gln Gly Val Lys Ser Asn
            260                 265                 270

Lys Gly Leu Asn Glu Gln Asp Lys Leu Ala Lys Thr Thr Glu Ile Gln
```

-continued

```
            275                 280                 285

Ala Gln Leu Asp Asp Leu Asp Arg Leu Asn Asn Ala Leu Ser Ala Met
    290                 295                 300

Ser Ser Val Ser Lys Ala Val Gln
305                 310

<210> SEQ ID NO 5
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Glu Gln Glu Lys Ala Leu Asn Phe Gly Ile Ile Ser Thr Glu Ser
1               5                   10                  15

Gln Gln Asn Leu Lys Pro Gln Trp Thr Pro Phe Leu Gln Asp Met Glu
            20                  25                  30

Lys Lys Leu Gly Val Lys Val Asn Ala Phe Phe Ala Pro Asp Tyr Ala
        35                  40                  45

Gly Ile Ile Gln Gly Met Arg Phe Asn Lys Val Asp Ile Ala Trp Tyr
    50                  55                  60

Gly Asn Leu Ser Ala Met Glu Ala Val Asp Arg Ala Asn Gly Gln Val
65                  70                  75                  80

Phe Ala Gln Thr Val Ala Ala Asp Gly Ser Pro Gly Tyr Trp Ser Val
            85                  90                  95

Leu Ile Val Asn Lys Asp Ser Pro Ile Asn Asn Leu Asn Asp Leu Leu
            100                 105                 110

Ala Lys Arg Lys Asp Leu Thr Phe Gly Asn Gly Asp Pro Cys Ser Thr
            115                 120                 125

Ser Gly Phe Leu Val Pro Gly Tyr Tyr Val Phe Ala Lys Asn Asn Ile
    130                 135                 140

Ser Ala Ser Asp Phe Lys Arg Thr Val Asn Ala Gly His Glu Thr Asn
145                 150                 155                 160

Ala Leu Ala Val Ala Asn Lys Gln Val Asp Val Ala Thr Asn Asn Thr
                165                 170                 175

Glu Asn Leu Asp Lys Leu Lys Thr Ser Ala Pro Glu Lys Leu Lys Glu
            180                 185                 190

Leu Lys Val Ile Trp Lys Ser Pro Leu Ile Pro Gly Asp Pro Ile Val
            195                 200                 205

Trp Arg Lys Asn Leu Ser Glu Thr Thr Lys Asp Lys Ile Tyr Asp Phe
    210                 215                 220

Phe Met Asn Tyr Gly Lys Thr Pro Glu Glu Lys Ala Val Leu Glu Arg
225                 230                 235                 240

Leu Gly Trp Ala Pro Phe Arg Ala Ser Ser Asp Leu Gln Leu Val Pro
                245                 250                 255

Ile Arg Gln Leu Ala Leu Phe Lys Glu Met Gln Gly Val Lys Ser Asn
            260                 265                 270

Lys Gly Leu Asn Glu Gln Asp Lys Leu Ala Lys Thr Thr Glu Ile Gln
        275                 280                 285

Ala Gln Leu Asp Asp Leu Asp Arg Leu Asn Asn Ala Leu Ser Ala Met
    290                 295                 300

Ser Ser Val Ser Lys Ala Val Gln
305                 310
```

-continued

```
<210> SEQ ID NO 6
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Lys Asn Ile Ala Phe Leu Leu Ala Ser Met Phe Val Phe Ser
1               5                   10                  15

Ile Ala Thr Asn Ala Tyr Ala Ser Asp Ile Gln Met Thr Gln Ser Pro
                20                  25                  30

Ser Ser Leu Ser Ala Ser Val Gly Asp Arg Val Thr Ile Thr Cys Arg
            35                  40                  45

Ala Ser Gln Ser Val Ser Ser Ala Val Ala Trp Tyr Gln Gln Lys Pro
        50                  55                  60

Gly Lys Ala Pro Lys Leu Leu Ile Tyr Ser Ala Ser Ser Leu Tyr Ser
65                  70                  75                  80

Gly Val Pro Ser Arg Phe Ser Gly Ser Arg Ser Gly Thr Asp Phe Thr
                85                  90                  95

Leu Thr Ile Ser Ser Leu Gln Pro Glu Asp Phe Ala Thr Tyr Tyr Cys
                100                 105                 110

Gln Gln Gly Tyr Gln Ser Leu Ile Thr Phe Gly Gln Gly Thr Lys Val
            115                 120                 125

Glu Ile Lys Arg Thr Val Ala Ala Pro Ser Val Phe Ile Phe Pro Pro
    130                 135                 140

Ser Asp Ser Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 7
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Lys Asn Ile Ala Phe Leu Leu Ala Ser Met Phe Val Phe Ser
1               5                   10                  15

Ile Ala Thr Asn Ala Tyr Ala Ser Asp Ile Gln Met Thr Gln Ser Pro
                20                  25                  30

Ser Ser Leu Ser Ala Ser Val Gly Asp Arg Val Thr Ile Thr Cys Arg
            35                  40                  45

Ala Ser Gln Ser Val Ser Ser Ala Val Ala Trp Tyr Gln Gln Lys Pro
        50                  55                  60
```

```
Gly Lys Ala Pro Lys Leu Leu Ile Tyr Ser Ala Ser Ser Leu Tyr Ser
65                  70                  75                  80

Gly Val Pro Ser Arg Phe Ser Gly Ser Arg Ser Gly Thr Asp Phe Thr
                85                  90                  95

Leu Thr Ile Ser Ser Leu Gln Pro Glu Asp Phe Ala Thr Tyr Tyr Cys
                100                 105                 110

Gln Gln Ser Ser Ser Ser Leu Ile Thr Phe Gly Gln Gly Thr Lys Val
            115                 120                 125

Glu Ile Lys Arg Thr Val Ala Ala Pro Ser Val Phe Ile Phe Pro Pro
        130                 135                 140

Ser Asp Ser Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 8
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Lys Asn Ile Ala Phe Leu Leu Ala Ser Met Phe Val Phe Ser
1                   5                   10                  15

Ile Ala Thr Asn Ala Tyr Ala Ser Asp Ile Gln Met Thr Gln Ser Pro
                20                  25                  30

Ser Ser Leu Ser Ala Ser Val Gly Asp Arg Val Thr Ile Thr Cys Arg
            35                  40                  45

Ala Ser Gln Ser Val Ser Ser Ala Val Ala Trp Tyr Gln Gln Lys Pro
        50                  55                  60

Gly Lys Ala Pro Lys Leu Leu Ile Tyr Ser Ala Ser Ser Leu Tyr Ser
65                  70                  75                  80

Gly Val Pro Ser Arg Phe Ser Gly Ser Arg Ser Gly Thr Asp Phe Thr
                85                  90                  95

Leu Thr Ile Ser Ser Leu Gln Pro Glu Asp Phe Ala Thr Tyr Tyr Cys
                100                 105                 110

Gln Gln Gly Gly Trp Trp Tyr Pro Ile Thr Phe Gly Gln Gly Thr Lys
            115                 120                 125

Val Glu Ile Lys Arg Thr Val Ala Ala Pro Ser Val Phe Ile Phe Pro
        130                 135                 140

Pro Ser Asp Ser Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190
```

-continued

```
Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```

```
<210> SEQ ID NO 9
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

```
Met Lys Lys Asn Ile Ala Phe Leu Leu Ala Ser Met Phe Val Phe Ser
1               5                   10                  15

Ile Ala Thr Asn Ala Tyr Ala Ser Asp Ile Gln Met Thr Gln Ser Pro
            20                  25                  30

Ser Ser Leu Ser Ala Ser Val Gly Asp Arg Val Thr Ile Thr Cys Arg
        35                  40                  45

Ala Ser Gln Ser Val Ser Ser Ala Val Ala Trp Tyr Gln Gln Lys Pro
    50                  55                  60

Gly Lys Ala Pro Lys Leu Leu Ile Tyr Ser Ala Ser Ser Leu Tyr Ser
65                  70                  75                  80

Gly Val Pro Ser Arg Phe Ser Gly Ser Arg Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Tyr Tyr His Met Tyr Pro Ile Thr Phe Gly Gln Gly Thr Lys
        115                 120                 125

Val Glu Ile Lys Arg Thr Val Ala Ala Pro Ser Val Phe Ile Phe Pro
        130                 135                 140

Pro Ser Asp Ser Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```

```
<210> SEQ ID NO 10
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

```
Met Lys Lys Asn Ile Ala Phe Leu Leu Ala Ser Met Phe Val Phe Ser
1               5                   10                  15
```

```
Ile Ala Thr Asn Ala Tyr Ala Ser Asp Ile Gln Met Thr Gln Ser Pro
            20                  25                  30

Ser Ser Leu Ser Ala Ser Val Gly Asp Arg Val Thr Ile Thr Cys Arg
            35                  40                  45

Ala Ser Gln Ser Val Ser Ser Ala Val Ala Trp Tyr Gln Gln Lys Pro
            50                  55                  60

Gly Lys Ala Pro Lys Leu Leu Ile Tyr Ser Ala Ser Ser Leu Tyr Ser
65                  70                  75                  80

Gly Val Pro Ser Arg Phe Ser Gly Ser Arg Ser Gly Thr Asp Phe Thr
                    85                  90                  95

Leu Thr Ile Ser Ser Leu Gln Pro Glu Asp Phe Ala Thr Tyr Tyr Cys
                100                 105                 110

Gln Gln Ser Ser Ser Ser Leu Ile Thr Phe Gly Gln Gly Thr Lys Val
            115                 120                 125

Glu Ile Lys Arg Thr Val Ala Ala Pro Ser Val Phe Ile Phe Pro Pro
    130                 135                 140

Ser Asp Ser Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                    165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 11
<211> LENGTH: 312
<212> TYPE: PRT
<213> ORGANISM: Escherichia coli

<400> SEQUENCE: 11

Glu Glu Gln Glu Lys Ala Leu Asn Phe Gly Ile Ile Ser Thr Glu Ser
1               5                   10                  15

Gln Gln Asn Leu Lys Pro Gln Trp Thr Pro Phe Leu Gln Asp Met Glu
            20                  25                  30

Lys Lys Leu Gly Val Lys Val Asn Ala Phe Phe Ala Pro Asp Tyr Ala
            35                  40                  45

Gly Ile Ile Gln Gly Met Arg Phe Asn Lys Val Asp Ile Ala Trp Tyr
        50                  55                  60

Gly Asn Leu Ser Ala Met Glu Ala Val Asp Arg Ala Asn Gly Gln Val
65                  70                  75                  80

Phe Ala Gln Thr Val Ala Ala Asp Gly Ser Pro Gly Tyr Trp Ser Val
                    85                  90                  95

Leu Ile Val Asn Lys Asp Ser Pro Ile Asn Asn Leu Asn Asp Leu Leu
                100                 105                 110

Ala Lys Arg Lys Asp Leu Thr Phe Gly Asn Gly Asp Pro Asn Ser Thr
            115                 120                 125

Ser Gly Phe Leu Val Pro Gly Tyr Tyr Val Phe Ala Lys Asn Asn Ile
    130                 135                 140

Ser Ala Ser Asp Phe Lys Arg Thr Val Asn Ala Gly His Glu Thr Asn
```

-continued

```
145                    150                     155                     160

Ala Leu Ala Val Ala Asn Lys Gln Val Asp Val Ala Thr Asn Asn Thr
                165                     170                     175

Glu Asn Leu Asp Lys Leu Lys Thr Ser Ala Pro Glu Lys Leu Lys Glu
                180                     185                     190

Leu Lys Val Ile Trp Lys Ser Pro Leu Ile Pro Gly Asp Pro Ile Val
                195                     200                     205

Trp Arg Lys Asn Leu Ser Glu Thr Thr Lys Asp Lys Ile Tyr Asp Phe
        210                     215                     220

Phe Met Asn Tyr Gly Lys Thr Pro Glu Glu Lys Ala Val Leu Glu Arg
225                     230                     235                     240

Leu Gly Trp Ala Pro Phe Arg Ala Ser Ser Asp Leu Gln Leu Val Pro
                245                     250                     255

Ile Arg Gln Leu Ala Leu Phe Lys Glu Met Gln Gly Val Lys Ser Asn
                260                     265                     270

Lys Gly Leu Asn Glu Gln Asp Lys Leu Ala Lys Thr Thr Glu Ile Gln
                275                     280                     285

Ala Gln Leu Asp Asp Leu Asp Arg Leu Asn Asn Ala Leu Ser Ala Met
        290                     295                     300

Ser Ser Val Ser Lys Ala Val Gln
305                     310
```

```
<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser His His His His His His
1                   5
```

```
<210> SEQ ID NO 13
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Phe Leu Leu Ala Ser Met Phe Val Phe Ser Ile Ala Thr Asn Ala Tyr
1                   5                   10                  15

Ala Glu Ile Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
        35                  40                  45

Phe Ser Tyr Ser Ser Ile His Trp Val Arg Gln Ala Pro Gly Lys Gly
        50                  55                  60

Leu Glu Trp Val Ala Ser Ile Ser Pro Tyr Tyr Gly Ser Thr Ser Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
                100                 105                 110

Val Tyr Tyr Cys Ala Arg Tyr Ser Asp Ser Val Gly Tyr Trp Tyr Ser
```

-continued

```
            115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Ser Arg His His His
                245                 250                 255

His His His
```

```
<210> SEQ ID NO 14
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Phe Leu Leu Ala Ser Met Phe Val Phe Ser Ile Ala Thr Asn Ala Tyr
1               5                   10                  15

Ala Glu Ile Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Phe Ser Ser Ser Ile His Trp Val Arg Gln Ala Pro Gly Lys Gly Leu
    50                  55                  60

Glu Trp Val Ala Ser Ile Ser Ser Ser Gly Ser Thr Ser Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Gln Trp Ser Ser Val Met Glu Trp Tyr Ile Gly
        115                 120                 125

Leu Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205

Ser Val Val Thr Val Pro Ser Ser Ser Leu Gly Thr Gln Thr Tyr Ile
```

```
        210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Ser Arg His His His His
                245                 250                 255

His His

<210> SEQ ID NO 15
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Phe Leu Leu Ala Ser Met Phe Val Phe Ser Ile Ala Thr Asn Ala Tyr
1                   5                   10                  15

Ala Glu Ile Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Val Ser Ser Tyr Ser Ile His Trp Val Arg Gln Ala Pro Gly Lys Gly
        50                  55                  60

Leu Glu Trp Val Ala Ser Ile Tyr Ser Ser Tyr Gly Tyr Thr Ser Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ala Arg Trp Ser Val Tyr Tyr Ser Ser Tyr Trp Lys
        115                 120                 125

Ala Met Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Ser Arg His His His
                245                 250                 255

His His His

<210> SEQ ID NO 16
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 16

Phe Leu Leu Ala Ser Met Phe Val Phe Ser Ile Ala Thr Asn Ala Tyr
1               5                   10                  15

Ala Glu Ile Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Val Ser Tyr Ser Ser Ile His Trp Val Arg Gln Ala Pro Gly Lys Gly
        50                  55                  60

Leu Glu Trp Val Ala Ser Ile Tyr Pro Ser Ser Gly Tyr Thr Ser Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
                100                 105                 110

Val Tyr Tyr Cys Ala Arg Gln Asp Tyr Phe Gly Trp Tyr Trp Lys Thr
            115                 120                 125

Ala Met Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Ser Arg His His His
            245                 250                 255

His His His

<210> SEQ ID NO 17
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Phe Leu Leu Ala Ser Met Phe Val Phe Ser Ile Ala Thr Asn Ala Tyr
1               5                   10                  15

Ala Glu Ile Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Phe Ser Ser Ser Ser Ile His Trp Val Arg Gln Ala Pro Gly Lys Gly
        50                  55                  60

Leu Glu Trp Val Ala Ser Ile Ser Ser Ser Ser Gly Ser Thr Ser Tyr
65                  70                  75                  80
```

-continued

```
Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ala Arg Gln Tyr Glu Ser Val Trp Asn Trp Tyr Ile
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Ser Arg His His His
                245                 250                 255

His His His
```

GLYPHOSATE BIOSENSOR

CROSS REFERENCE TO RELATED APPLICATIONS

This application is a U.S. national counterpart application of international application serial No. PCT/US2020/044697 filed Aug. 3, 2020, which claims priority under 35 U.S.C. § 119 (e) to U.S. Provisional Application Ser. No. 62/881,393 filed Aug. 1, 2019, the disclosures of which are incorporated herein by reference.

INCORPORATION BY REFERENCE OF MATERIAL SUBMITTED ELECTRONICALLY

The instant application contains a Sequence Listing which has been submitted electronically in ASCII format and is hereby incorporated by reference in its entirety. Said ASCII copy, created on Aug. 12, 2020, is named 29920-321771 SL.txt and is 39,849 bytes in size.

BACKGROUND

Glyphosate is a phosphonate that is the active ingredient in the herbicide ROUNDUP used to kill weeds by blocking pathways essential to plant growth. Currently, glyphosate is the most popular herbicide used around the globe. It has been recently classified as a probable carcinogen. Glyphosate also has made recent headlines for its widespread use on genetically modified seeds with research that links it to antibiotic resistance and hormone disruption. Glyphosate is also considered a potential environmental hazard. Several states are planning to restrict its use, while it has already been banned in the state of California. Hence, there is a need for the development of reliable detection methods for glyphosate in the soil, rivers, and drinking water. This can help determine its concentration and effect on the environment.

When *E. coli* is in an environment that is phosphorus-deficient, the pho regulon in the bacteria turns on transcription of the phn operon, which codes for a number of proteins including EcPhnD or *E. coli* Phosphate-binding protein. This protein is able to bind many phosphonates and allows their uptake by the bacteria for use as a phosphorus source. Naturally, PhnD binds to 2-Aminoethyl Phosphonate (2-AEP) with very high binding affinity, with a $K_d$ of about 5 nM. However, previous research found that EcPhnD could bind glyphosate but with very low affinity, in fact the $K_d$ for glyphosate is around 650 μM. Upon binding to a ligand, all members of the periplasmic binding protein superfamily undergo a large conformational change from an open to a closed structure. Thus, the EcPhnD could serve as a scaffold for developing a biosensor to detect glyphosate.

SUMMARY

The disclosure relies upon site directed mutagenesis to engineer the binding pocket of EcPhnD mutants to accommodate glyphosate while retaining the large change in fluorescence associated with the conformational change from the open to the closed form. The engineered protein produces a biosensor capable of binding to glyphosate with a higher binding affinity than the wildtype protein.

The disclosed glyphosate biosensor offers several advantages. First, the biosensor is reagentless, that is, no consumable reagent or substrate is required. This is a particular advantage over current sensing methods that employ ELISA or enzyme-based detection that require a consumable substrate. Second, no standard curve is required since the $K_d$ value is stable over different measurements. Third, no separation, chromatography or special sample treatment is required before using the sensor other than the addition of a working buffer to maintain an appropriate pH. Since binding of glyphosate to the protein is an equilibrium process, the sensor described here can be reused by removing the bound ligand (i.e., glyphosate) through dialysis. Additionally, only nanomolar concentrations of the protein are required for the detection of glyphosate due to the increase in binding affinity as a result of the engineered amino acid sequence.

In some embodiments, the disclosure provides a modified binding pocket of PhnD.

In some embodiments, an engineered protein biosensor having an N-terminal and a C-terminal is disclosed comprising: (i) an amino acid sequence comprising 312 amino acids and having at least a 90% sequence identity to SEQ ID NO: 1; and (ii) a fluorescent reporter coupled to the amino acid at position 126 of the engineered protein.

In some embodiments, an engineered protein biosensor having an N-terminal and a C-terminal is disclosed comprising: (i) an amino acid sequence comprising 312 amino acids and having at least a 95% sequence identity to SEQ ID NO: 1; wherein the amino acid at position 177 is an asparagine and the amino acid at position 126 is a cysteine; and (ii) a fluorescent reporter is covalently bound to the amino acid at position 126 of the engineered protein.

In some embodiments, an engineered protein biosensor having an N-terminal and a C-terminal is disclosed comprising: (i) an amino acid sequence having at least a 90% sequence identity to *E. coli* periplasmic binding protein (EcPhnD); and (ii) a fluorescent reporter coupled to the amino acid sequence.

Embodiments of the invention are further described by the following enumerated clauses. It will be understood that any of the embodiments described herein can be used in connection with any other embodiments described herein to the extent that the embodiments do not contradict one another.

Clause 1. An engineered protein biosensor having an N-terminal and a C-terminal comprising:
(i) an amino acid sequence comprising 312 amino acids and having at least a 90% sequence identity to SEQ ID NO: 1; and
(ii) a fluorescent reporter coupled to the amino acid at position 126 of the engineered protein.

Clause 2. The engineered protein of clause 1, wherein the amino acid at position 177 is an asparagine.

Clause 3. The engineered protein of clause 1 or 2, wherein the amino acid at position 126 is a cysteine.

Clause 4. The engineered protein of clause 1-3, wherein the amino acid sequence has at least a 95% sequence identity to SEQ ID NO: 1.

Clause 5. The engineered protein of clause 1-3, wherein the amino acid sequence has at least a 98% sequence identity to SEQ ID NO: 1.

Clause 6. The engineered protein of clause 1-3, wherein the amino acid sequence is SEQ ID NO: 1.

Clause 7. The engineered protein of clause 1-6, wherein the fluorescent reporter is selected from the group consisting of acrylodan, Coumarin (also referred to as (7-Diethylamino-3-(4'-Maleimidylphenyl)-4-Methyl-coumarin)), danzyl aziridine, 4-[N-[(2-iodoacetoxy)ethyl]-N-methylamino]-7-nitrobenz-2-oxa-1,3-diazole ester (IANBDE), 4-N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670

LSS dye, Texas Red, C5-Bromoacetamide, Alexa Fluor 750 C5-maleimide, and BODIPY 577/618.

Clause 8. The engineered protein of clause 1-6, wherein the fluorescent reporter is acrylodan or Coumarin.

Clause 9. The engineered protein of clause 1-8, wherein the fluorescent reporter is covalently linked to a cysteine at amino acid position 126 of the amino acid sequence.

Clause 10. The engineered protein of clause 1-9, wherein the C-terminal comprises a modification of truncating the last nine amino acids.

Clause 11. An engineered protein biosensor having an N-terminal and a C-terminal comprising:
(i) an amino acid sequence comprising 312 amino acids and having at least a 95% sequence identity to SEQ ID NO: 1; wherein the amino acid at position 177 is an asparagine and the amino acid position at 126 is a cysteine; and
(ii) a fluorescent reporter covalently bound to the amino acid at position 126 of the amino acid sequence.

Clause 12. An engineered protein biosensor having an N-terminal and a C-terminal comprising:
(i) an amino acid sequence having at least a 90% sequence identity to E. coli periplasmic binding protein EcPhnD; and
(ii) a fluorescent reporter coupled to the amino acid sequence.

Clause 13. The engineered protein of clause 12, wherein the protein comprises at least 300 amino acids and position 177 is an asparagine.

Clause 14. The engineered protein of clause 12 or 13, wherein the protein comprises at least 300 amino acids and position 126 is a cysteine.

Clause 15. The engineered protein of clause 14, wherein the fluorescent reporter is coupled to the cysteine at amino acid position 126.

Clause 16. The engineered protein of clause 11 or 15, wherein the fluorescent reporter is selected from the group consisting of acrylodan, Coumarin (7-Diethyl-amino-3-(4'-Maleimidylphenyl)-4-Methylcoumarin), danzyl aziridine, 4-[N-[(2-iodoacetoxy)ethyl]-N-meth-ylamino]-7-nitrobenz-2-oxa-1,3-diazole ester (IANBDE), 4-N-[(2-iodoacetoxy)ethyl]-N-methyl-amino-7-nitrobenz-2-oxa-1,3-diazole (IANBDA), Texas Red C2-Maleimide, Lucifer yellow iodoacet-amide, Alexafluor 680 maleimide, Kodak X-Sight 670 LSS dye, Texas Red, C5-Bromoacetamide, Alexa Fluor 750 C5-maleimide, and BODIPY 577/618. Clause 17. The engineered protein of clause 11 or 16, wherein the fluorescent reporter is acrylodan or Coumarin.

Clause 18. The engineered protein of clause 12-17, wherein the amino acid sequence has at least 95% sequence identity to EcPhnD.

Clause 19. The engineered protein of clause 12-18, wherein the amino acid sequence has at least 98% sequence identity to EcPhnD.

Clause 20. The engineered protein of clause 12-19, wherein the amino acid sequence has at least 95% sequence identity to EcPhnD, and amino acid position 177 is an asparagine and amino acid position 126 is a cysteine.

Clause 21. The clauses of any one of 1-20, wherein the engineered protein further comprises an antibody fragment.

Clause 22. The clauses of any one of 1-20, wherein the C-terminal comprises a marker.

Clause 23. The clause of anyone of 1-22, wherein the C-terminal comprises a histidine tag.

Clause 24. The clauses of any one of 1-21, wherein the C-terminal comprises a modification.

Clause 25. The clauses of any one of 1-24, wherein the C-terminal is truncated.

Clause 26. The clause of any one of 1-25, wherein the last 9 amino acids of the C-terminal are truncated.

Clause 27. The clauses of any one of 1-26, wherein the C-terminal is modified to prevent dimerization.

Clause 28. A method of detecting glyphosate comprising: (i) contacting a sample with a biosensor; and (ii) detecting the presence of glyphosate.

Clause 29. The method of clause 28, wherein the biosensor comprises an engineered protein comprising an amino acid sequence having at least 90% sequence identity to SEQ ID NO: 1, and wherein amino acid position 177 is an asparagine and amino acid position 126 is a cysteine, and wherein a reporter is coupled to the cysteine at position 126.

Clause 30. The method of clause 29, wherein the reporter is selected from the group consisting of acrylodan, Coumarin (7-Diethylamino-3-(4'-Maleimidylphenyl)-4-Methylcoumarin), danzyl aziridine, 4-[N-[(2-iodoac-etoxy)ethyl]-N-methylamino]-7-nitrobenz-2-oxa-1,3-diazole ester (IANBDE), 4-N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas Red, C5-Bromoacet-amide, Alexa Fluor 750 C5-maleimide, and BODIPY 577/618.

Clause 31. The method of clause 29 or 30, wherein the step of detecting comprises exposing the then engineered protein biosensor to a light to excite the reporter and visualizing a signal from the reporter by detecting an emitted wavelength.

Clause 32. The method of clause 28-31, wherein the step of visualizing comprises irradiating the engineered protein with an excitation wavelength light and detecting light emitted from the engineered protein at an emission wavelength, and wherein there is a shift in the emitted light when glyphosate is present compared to when no glyphosate is present.

Clause 33. The method of any one of clause 29-32, further comprising contacting the engineered protein biosensor with an antibody fragment, wherein the antibody fragment is configured to bind to the engineered protein when it is bound to glyphosate.

Clause 34. The method of any one of clause 28-33, wherein the method does not require a consumable reagent or substrate.

Clause 35. The method of any one of clauses 28-34, further comprising the step of dialyzing the engineered protein biosensor to remove the ligand making the biosensor reusable.

Clause 36. The engineered protein of clauses 1-35, wherein the engineered protein biosensor undergoes a confirmation change upon the binding of glyphosate.

Clause 37. The method of any one of clauses 28-36, wherein the sample comprises a solid, liquid, gas, or a combination thereof.

Clause 38. The engineered protein of clause 37, wherein the sample comprises soil or water.

Clause 39. The method of any one of clauses 28-38, further comprising immobilizing the engineered protein on a substrate.

Clause 40. The method of any one of clause 32-39, wherein a shift in the wavelength correlates to the concentration of glyphosate in the sample.

Clause 41. The engineered protein of any of one clauses 1-27, wherein the amino acid sequence is SEQ ID NO: 1.

Clause 42. The engineered protein of any one of clauses 1-27, wherein the amino acid sequence is SEQ ID NO: 2.

Clause 43. The engineered protein of any one of clauses 1-27, wherein the amino acid sequence is SEQ ID NO: 3.

Clause 44. The engineered protein of any one of clauses 1-27, wherein the amino acid sequence is SEQ ID NO: 4.

Clause 45. The engineered protein of any one of clauses 1-27, wherein the amino acid sequence is SEQ ID NO:5.

Clause 46. The method of clause 33, wherein the antibody is fragment is selected from the group consisting of Fab N1, Fab N2, Fab N3, Fab N 4, and Fab N5.

DETAILED DESCRIPTION

Definitions

Figure 1:
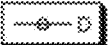
FIG. 1 shows titration of PND2 177NΔ with glyphosate (left), and titration of PND2 177NΔ+Fab N2 with glyphosate (right)
Figure 1:
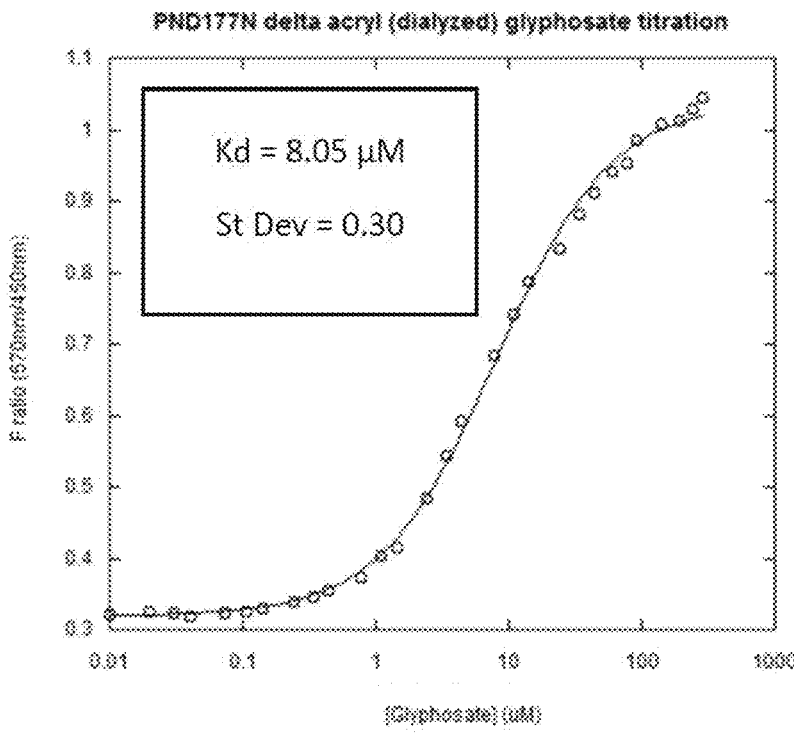
Figure 1:
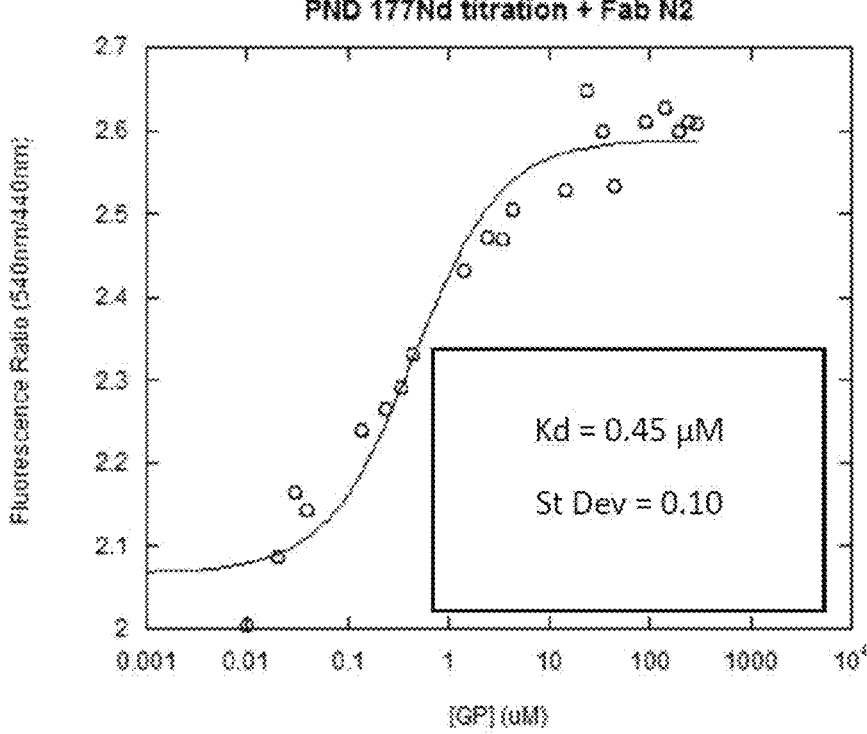

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, WI), ChemPep Inc. (Miami, FL), and Genzyme Pharmaceuticals (Cambridge, MA). Atypical amino acids may be purchased from commercial suppliers, synthesized de novo, or chemically modified or derivatized from naturally occurring amino acids.

Embodiments

Embodiments of the invention includes biosensors for the detection of glyphosate in a sample. In some embodiments, the biosensor utilizes a variant *E. coli* periplasmic binding protein (EcPhnD) wherein the amino acid at position 177 of the variant EcPhnD protein has been mutated to an asparagine and where the amino acid at position 126 has been mutated to a cysteine. In some embodiments, an engineered protein biosensor comprises an amino acid sequence of SEQ ID NO: 1. In other embodiments the engineered protein comprises an amino acid sequence having at least 90% sequence identity to SEQ ID. NO: 1; and wherein a reporter group is coupled to a cysteine residue at position 126 of the engineered protein. In some embodiments, the engineered protein further includes a C-terminal modification. In some embodiments, the C-terminal modification comprises a C-terminal marker. In an illustrative embodiment, the C-terminal marker is a histidine tag. In other embodiments, the engineered protein comprises a C-terminally truncated protein that lacks all or a portion of the C-terminal residues involved in dimerization. In an illustrative embodiment, the C-terminally truncated protein lacks its C-terminal 9 amino acids.

In some embodiments, the reporter group is a fluorophore. The fluorophore may be coupled to the cysteine residue at position 126 of the engineered protein. The fluorophore may be acrylodan, danzyl aziridine, 4-[N-[(2-iodoacetoxy)ethyl]-N-methylamino]-7-nitrobenz-2-oxa-1,3-diazole ester (IANBDE), 4-N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas Red, C5-Bromoacetamide, Alexa Fluor 750 C5-maleimide, or BODIPY 577/618.

In some embodiments, the method of using the biosensor is reagentless. In other embodiments, the method further includes an antibody fragment that binds specifically to the closed glyphosate-bound form of the engineered protein biosensor.

Biosensor

Disclosed herein are glyphosate biosensors comprising engineered proteins each coupled to a reporter. In some embodiments, an engineered protein biosensor is disclosed having an N-terminal and a C-terminal comprising: (i) an amino acid sequence having at least a 90% sequence identity to *E. coli* periplasmic binding protein (EcPhnD); and (ii) a fluorescent reporter coupled to the amino acid sequence.

In some embodiments, the engineered protein biosensor comprises an amino acid sequence having a sequence identity of at least 85%, 86%, 87%, 88% 89%, 90%, 91%, 92%, 93%, 94%, 95%, 96%, 97%, 98%, or 99% to EcPhnD (SEQ ID NO: 11). In some embodiments, the engineered protein biosensor comprises an amino acid sequence having a sequence identity of between about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99%, about 98% to about 99%, about 90% to about 98%, about 90% to about 97%, about 90% to about 96%, about 90% to about 95%, about 95% to about 98%, or about 95% to about 97% to EcPhnD. In some embodiments, the engineered protein biosensor comprises an amino acid sequence having a sequence identity of up to 99%, up to 98%, up to 97%, up to 96%, up to 95%, up to 94%, up to 93%, up to 92%, up to 91%, or up to 90% to EcPhnD.

In some embodiments, the engineered protein biosensor having an N-terminal and a C-terminal comprises an amino acid sequence having a 90% sequence identity to EcPhnD. In some embodiments, the engineered protein biosensor comprises an amino acid sequence having a 95% sequence identity to EcPhnD. In some embodiments, the engineered protein biosensor comprises an amino acid sequence having a 97% sequence identity to EcPhnD. In some embodiments, the engineered protein biosensor comprises an amino acid sequence having a 98% sequence identity to EcPhnD. In some embodiments, the engineered protein biosensor comprises an amino acid sequence having a 99% sequence identity to EcPhnD. In some embodiments, the engineered protein biosensor comprises an amino acid sequence having a 100% sequence identity to EcPhnD.

In some embodiments, the engineered protein biosensor having an N-terminal and a C-terminal comprises an amino acid sequence of at least 290, 295, 300, 305, 310, 315, or 320 amino acids. In some embodiments, the amino acid sequence comprises between 290 and 320 amino acids, between 295 and 315 amino acids, between 300 and 315 amino acids, between 305 and 315 amino acids, or between 310 and 315 amino acids. In some embodiments, the engineered protein biosensor comprises 300, 305, 310, 312, or 315 amino acids. In some embodiments, the amino acid sequence comprises at least 300 amino acids. In some embodiments, the amino acid sequence comprises 312 amino acids.

In some embodiments, the engineered protein biosensor having an N-terminal and a C-terminal comprises (i) an amino acid sequence of 312 amino acids having at least a 90% sequence identity to SEQ ID NO: 1, and (ii) a reporter coupled to the amino acid sequence. In some embodiments, the engineered protein biosensor comprises an amino acid sequence having a sequence identity of at least 85%, 86%, 87%, 88% 89%, 90%, 91%, 92%, 93%, 94%, 95%, 96%, 97%, 98%, or 99% to SEQ ID NO: 1. In some embodiments, the engineered protein biosensor comprises an amino acid sequence having a sequence identity of between about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99%, about 98% to about 99%, about 90% to about 98%, about 90% to about 97%, about 90% to about 96%, about 90% to about 95%, about 95% to about 98%, or about 95% to about 97% to SEQ ID NO: 1. In some embodiments, the engineered protein biosensor comprises an amino acid sequence having a sequence identity of up to 99%, up to 98%, up to 97%, up to 96%, up to 95%, up to 94%, up to 93%, up to 92%, up to 91%, or up to 90% to SEQ ID NO: 1.

In some embodiments, the engineered protein biosensor comprises an amino acid sequence having at least 95% sequence identity to SEQ ID NO: 1. In some embodiments, the engineered protein biosensor comprises an amino acid sequence having a 95% sequence identity to SEQ ID NO: 1. In some embodiments, the engineered protein biosensor having an N-terminal and a C-terminal comprises an amino acid sequence having a 90% sequence identity to SEQ ID NO: 1. In some embodiments, the engineered protein biosensor comprises an amino acid sequence having a 95% sequence identity to SEQ ID NO: 1. In some embodiments, the engineered protein biosensor comprises an amino acid sequence having a 97% sequence identity to SEQ ID NO: 1. In some embodiments, the engineered protein biosensor comprises an amino acid sequence having a 98% sequence identity to SEQ ID NO: 1. In some embodiments, the engineered protein biosensor comprises an amino acid sequence having a 99% sequence identity to SEQ ID NO: 1. In some embodiments, the engineered protein biosensor comprises an amino acid sequence having a 100% sequence identity to SEQ ID NO: 1.

In some embodiments, the amino acid sequence comprises 312 amino acids having at least a 90% sequence identity to SEQ ID NO: 1, and wherein the amino acid is asparagine at position 177 of the amino acid sequence. In some embodiments, the amino acid is cysteine at position 126. In some embodiments, the amino acid sequence comprises 312 amino acids having at least a 90% sequence identity to SEQ ID NO: 1, and wherein the amino acid is asparagine at position 177 and the amino acid is cysteine at position 126 of the amino acid sequence.

In some embodiments, the engineered protein biosensor having an N-terminal and a C-terminal comprises (i) an amino acid sequence comprising 312 amino acids having at least a 90% sequence identity to SEQ ID NO:1, and wherein the amino acid position 177 is an asparagine and amino acid position 126 is a cysteine, and (ii) a reporter coupled to the amino acid sequence. In some embodiments, the amino acid sequence comprising 312 amino acids having at least 92% sequence identity to SEQ ID NO: 1, and wherein the amino acid position 177 is an asparagine and amino acid position 126 is a cysteine, and (ii) a reporter coupled to the amino acid sequence. In some embodiments, the amino acid sequence comprising 312 amino acids having at least 95% sequence identity to SEQ ID NO: 1, and wherein the amino acid position 177 is an asparagine and amino acid position 126 is a cysteine, and (ii) a reporter coupled to the amino acid sequence. In some embodiments, the amino acid sequence comprising 312 amino acids having at least 97% sequence identity to SEQ ID NO: 1, and wherein the amino acid position 177 is an asparagine and amino acid position 126 is a cysteine, and (ii) a reporter coupled to the amino acid sequence. In some embodiments, the amino acid sequence comprising 312 amino acids having at least 98% sequence identity to SEQ ID NO: 1, and wherein the amino acid position 177 is an asparagine and amino acid position 126 is a cysteine, and (ii) a reporter coupled to the amino acid sequence. In some embodiments, the amino acid sequence comprising 312 amino acids having at least 99% sequence identity to SEQ ID NO: 1, and wherein the amino acid position 177 is an asparagine and amino acid position 126 is a cysteine, and (ii) a reporter coupled to the amino acid sequence.

In some embodiments, the reporter is coupled to the cysteine at position 126. In some embodiment, the reporter is covalently bound to the cysteine at position 126.

In some embodiments, the engineered protein biosensor having an N-terminal and a C-terminal comprises (i) an amino acid sequence comprising 312 amino acids and having at least a 95% sequence identity to SEQ ID NO: 1; wherein the amino acid at position 177 is an asparagine and the amino acid at position 126 is a cysteine; and (ii) a reporter coupled to the amino acid at position 126 of the amino acid sequence.

In some embodiments, the amino acid sequence further comprises a modification to the C-terminal of the engineered protein. In some embodiments, the C-terminal is truncated to remove the ability of the protein to form a dimer. In some embodiments, the C-terminal is truncated to remove the last nine amino acids of the amino acid sequence. In some embodiments, the C-terminal further comprises a maker. In some embodiments, the marker is a histidine tag.

In some embodiments, the reporter is a fluorescent reporter. In some embodiments, the fluorescent reporter is selected from the group consisting of acrylodan, Coumarin (referred to as (7-Diethylamino-3-(4'-Maleimidylphenyl)-4-Methylcoumarin)), danzyl aziridine, 4-[N-[(2-iodoacetoxy)ethyl]-N-methylamino]-7-nitrobenz-2-oxa-1,3-diazole ester (IANBDE), 4-N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas Red, C5-Bromoacetamide, Alexa Fluor 750 C5-maleimide, and BODIPY 577/618. In some embodiments, the fluorescent reporter is acrylodan or Coumarin.

In some embodiments, the reporter is coupled to the amino acid sequence. In some embodiments, the reporter is covalently bound to the amino acid sequence. In some embodiments, the reporter is covalently bound to the cysteine at position 126 of the amino acid sequence. In some embodiments, the fluorescent reporter is coupled to the amino acid sequence of the engineered protein. In some embodiments, acrylodan is covalently bound to the cysteine at position 126 of the amino acid sequence of the engineered protein biosensor. In some embodiments, Coumarin is covalently bound to the cysteine at position 126 of the amino acid sequence of the engineered protein biosensor.

In some embodiments, an engineered protein biosensor having an N-terminal and a C-terminal, comprises (i) an amino acid sequence having 312 amino acids having at least a 95% sequence identity to SEQ ID NO:1, wherein the amino acid at position 177 is an asparagine and the amino acid at position 126 is a cysteine; and (ii) an acrylodan covalently bound to the cysteine at position 126.

In some embodiments, an engineered protein biosensor having an N-terminal and a C-terminal, comprises (i) an amino acid sequence having 312 amino acids having at least a 95% sequence identity to SEQ ID NO:1, wherein the amino acid at position 177 is an asparagine and the amino acid at position 126 is a cysteine; and (ii) a coumarin covalently bound to the cysteine at position 126.

Method of Detecting Glyphosate with the Biosensor

In some embodiments, a method of detecting glyphosate comprises (i) contacting a sample with an engineered protein biosensor comprising (a) an amino acid sequence and (b) a reporter coupled to the amino acid sequence; and (ii) visualizing the sample for the presence of glyphosate. In some embodiments, a method of detecting glyphosate comprises (i) contacting a sample with an engineered protein biosensor comprising (a) an amino acid sequence and (b) a reporter coupled to the amino acid sequence; (ii) irradiating or exposing the engineered protein biosensor to a light of a wavelength that can excite the reporter; and (iii) detecting the wavelength emitted from the excited reporter. In some embodiments, the detected emitted wavelength will change depending on whether glyphosate is present in the sample. In some embodiments, a shift in the wavelength emitted correlates to the concentration of glyphosate in the sample.

In some embodiments, the method further comprises contacting the engineered protein with an antibody fragment, wherein the antibody fragment is configured to bind to the engineered protein when it is bound to glyphosate. In some embodiments, the method comprises (i) contacting a sample with an engineered protein biosensor comprising (a) an amino acid sequence and (b) a reporter coupled to the amino acid sequence; (ii) providing an antibody fragment configured to bind to the engineered protein biosensor when the engineered protein biosensor is in the closed form configuration; and (iii) detecting the glyphosate bound engineered protein biosensor, wherein the step of detecting occurs through (a) irradiating the sample with light and visualizing the emitted wavelength or (b) an ELISA or universal flow assay. These and other methods that are commonly employed to detect a fluorescent dye, an antibody, or both are to be considered within the scope of the disclosed methods.

In some embodiments, the antibody fragment may be selected from the group consisting of Fab N1 (SEQ ID NO: 6), Fab N2 (SEQ ID NO: 7), Fab N3 (SEQ ID NO: 8), Fab N4 (SEQ ID NO: 9), and Fab N5 (SEQ ID NO: 10). In some embodiments, the antibody fragment is Fab N1. In some embodiments, the antibody fragment is Fab N2. In some embodiments, the antibody fragment is Fab N3. In some embodiments, the antibody fragment is Fab N4. In some embodiments, the antibody fragment is Fab N5. In some embodiments, the antibody fragment is comprises a combination of any one of Fab N1, Fab N2, Fab N3, Fab N4, or Fab N5. In one illustrative embodiment, the antibody fragment is Fab N2.

In some embodiments, the method does not require a consumable reagent or substrate. In some embodiments, the method further comprises the step of dialyzing the engineered protein to remove the ligand making the biosensor reusable. In this embodiment, the ligand is glyphosate. In some embodiments, the engineered protein biosensor is configured to undergo a conformational change when binding glyphosate, that is, from an open to a closed position.

In some embodiments, the sample comprises a solid, liquid, gas, or a combination thereof. In some embodiments, the sample comprises soil or water.

In some embodiments, the method further comprises immobilizing the engineered protein biosensor on a substrate.

```
SEQUENCES
PhnD 177N
                                                        SEQ ID NO: 1
EEQEKALNFG IISTESQQNL KPQWTPFLQD MEKKLGVKVN AFFAPDYAGI IQGMRFNKVD

IAWYGNLSAM EAVDRANGQV FAQTVAADGS PGYWSVLIVN KDSPINNLND LLAKRKDLTF

GNGDFCSTSG FLVPGYYVFA KNNISASDFK RTVNAGHETN ALAVANKQVD VATNNTNNID

KLKTSAPEKL KELKVIWKSP LIPGDPIVWRKNLSETTKDK IYDFFMNYGK TPEEKAVLER

LGWAPFRASS DLQLVPIRQL ALFKEMQGVK SNKGLNEQDK LAKTTEIQAQ LDDLDRLNNA

LSAMSSVSKA VQ

PhnD E177NΔ
                                                        SEQ ID NO: 2
EEQEKALNFG IISTESQQNL KPQWTPFLQD MEKKLGVKVN AFFAPDYAGI IQGMRFNKVD

IAWYGNLSAM EAVDRANGQV FAQTVAADGS PGYWSVLIVN KDSPINNLND LLAKRKDLTF

GNGDFCSTSG FLVPGYYVFA KNNISASDFK RTVNAGHETN ALAVANKQVD VATNNTNNLD

KLKTSAPEKL KELKVIWKSP LIPGSPIVWR KNLSETTKDK IYDFFMNYGK TPEEKAVLER

LGWAPFRASS DLQLVPIRQL ALFKEMQGVK SNKGLNEQDK LAKTTEIQAQ LDDLDRLNNA LSA

PhnD E177N, D205S
                                                        SEQ ID NO: 3
EEQEKALNFG IISTESQQNI KPQWTPFLQD MEKKLGVKVN AFFAPDYAGI IQGMRFNKVD

IAWYGNLSAM EAVDRANGQV FAQTVAADGS PGYWSVLIVN KDSPINNLND LLAKRKDLTF

GNGDFCSTSG FLVPGYYVFA KNNISASDFK RTVNAGHETN ALAVANKQVD VATNNTNNLD

KLKTSAPEKL KELKVIWKSP LIPGSPIVWR KNLSETTKDK IYDFFMNYGK TPEEKAVLER

LGWAPFRASS DLQLVPIRQL ALFKEMQGVK SNKGLNEQDK LAKTTEIQAQ LDDLDRLNNA

LSAMSSVSKA VQ

PhnD D205N
                                                        SEQ ID NO: 4
EEQEKALNFG IISTESQQNL KPQWTPFLQD MEKKLGVKVN AFFAPDYAGI IQGMRFNKVD

IAWYGNLSAM EAYDRANGQV FAQTVAADGS PGYWSVLIVN KDSPINNLND LLAKRKDLTF

GNGDFCSTSG FLVPGYYVFA KNNISASDFK RTVNAGEETN ALAVANKQVD VATNNTENLD

KLKTSAPEKL KELKVIWKSP LIPGNPIVWR KNLSETTKDK IYDFFMNYGK TPEEKAVLER

LGWAPFRASS DLQLVPIRQL ALFKEMQGVK SNKGLNEQDK LAKTTEIQAQ LDDLDRLNNA

LSAMSSVSKA VQ

Wild Type EcPhnD with a 126 C modification
                                                        SEQ ID NO: 5
EEQEKALNFG IISTESQQNL KPQWTPFLQD MEKKLGVKVN AFFAPDYAGI IQGMRFNKVD

IAWYGNLSAM EAVDRANGQV FAQTVAADGS PGYWSVLIVN KDSPINNLND LLAKRKDLTF

GNGDFCSTSG FLVPGYYVFA KNNISASDFK RTVNAGRETN AIAYANKQVD VATNNTENLD

KLKTSAPEKL KELKVIWKSP LIPGDPIVWR KNLSETTKDK IYDFFMNYGK TPEEKAVLER

LGWAPFRASS DLQLVPIRQL ALFKEMQGVK SNKGLNEQDK LAKTTEIQAQ LDDLDRLNNA

LSAMSSVSKA VQ
```

-continued

Fab N1
                                                        SEQ ID NO: 6
Light chain:
MKKNIAFLLASMFVFSIATNAYASDIQMTQSPSSLSASVGDRVTITCRASQSVSSAVAWYQQKPGKAPKLLI

YSASSLYSGVPSRFSGSRSGTDFTLTISSLQPEDFATYYCQQGYQSLITFGQGTKVEIKRTVAAPSVFIFPP

SDSQLKSGTASVVCLLNNFYPREAKVQWKVDNALQSGNSQESVTEQDSKDSTYSLSSTLTLSKADYEKHKVY

ACEVTHQGLSSPVTKSFNRGEC

Heavy chain:
FLLASMFVFSIATNAYAEISEVQLVESGGGLVQPGGSLRLSCAASGFNFSYSSIHWVRQAPGKGLEWVASIS

PYYGSTSYADSVKGRFTISADTSKNTAYLQMNSLRAEDTAVYYCARYSDSVGYWYSGLDYWGQGTLVTVSSA

STKGPSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTSRHHHHHH

Fab N2
                                                        SEQ ID NO: 7
Light chain:
MKKNIAFLLASMFVFSIATNAYASDIQMTQSPSSLSASVGDRVTITCRASQSVSSAVAWYQQKPGKAPKLLI

YSASSLYSGVPSRFSGSRSGTDFTLTISSLQPEDFATYYCQQSSSSLITFGQGTKVEIKRTVAAPSVFIFPP

SDSQLKSGTASVVCLLNNFYPREAKVQWKVDNALQSGNSQESVTEQDSKDSTYSLSSTLTLSKADYEKHKVY

ACEVTHQGLSSPVTKSFNRGEC

Heavy chain:
FLLASMFVFSIATNAYAEISEVQLVESGGGLVQPGGSLRLSCAASGFNFSSSIHWVRQAPGKGLEWVASISS

SSGSTSYADSVKGRFTISADTSKNTAYLQMNSLRAEDTAVYYCARQWSSVMEWYIGLDYWGQGTLVTVSSAS

TKGPSVFPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTSRHHHHHH

Fab N3
                                                        SEQ ID NO: 8
Light chain:
MKKNIAFLLASMFVFSIATNAYASDIQMTQSPSSLSASVGDRVTITCRASQSVSSAVAWYQQKPGKAPKLLI

YSASSLYSGVPSRFSGSRSGTDFTLTISSLQPEDFATYYCQQGGWWYPITFGQGTKVEIKRTVAAPSVFIFP

PSDSQLKSGTASVVCLLNNFYPREAKVQWKVDNALQSGNSQESVTEQDSKDSTYSLSSTLTLSKADYEKHKV

YACEVTHQGLSSPVTKSFNRGEC

Heavy chain:
FLLASMFVFSIATNAYAEISEVQLVESGGGLVQPGGSLRLSCAASGFNVSSYSIHWVRQAPGKGLEWVASIY

SSYGYTSYADSVKGRFTISADTSKNTAYLQMNSLRAEDTAVYYCARWSVYYSSYWKAMDYWGQGTLVTVSSA

STKGPSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTSRHHHHHH

Fab N4
                                                        SEQ ID NO: 9
Light chain:
MKKNIAFLLASMFVFSIATNAYASDIQMTQSPSSLSASVGDRVTITCRASQSVSSAVAWYQQKPGKAPKLLI

YSASSLYSGVPSRFSGSRSGTDFTLTISSLQPEDFATYYCQQYYHMYPITFGQGTKVEIKRTVAAPSVFIFP

PSDSQLKSGTASVVCLLNNFYPREAKVQWKVDNALQSGNSQESVTEQDSKDSTYSLSSTLTLSKADYEKHKV

YACEVTHQGLSSPVTKSFNRGEC

Heavy chain:
FLLASMFVFSIATNAYAEISEVQLVESGGGLVQPGGSLRLSCAASGFNVSYSSIHWVRQAPGKGLEWVASIY

PSSGYTSYADSVKGRFTISADTSKNTAYLQMNSLRAEDTAVYYCARQDYFGWYWKTAMDYWGQGTLVTVSSA

STKGPSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTSRHHHHHH

-continued

Fab N5

SEQ ID NO: 10

Light chain:
MKKNIAFLLASMFVFSIATNAYASDIQMTQSPSSLSASVGDRVTITCRASQSVSSAVAWYQQKPGKAPKLLI

YSASSLYSGVPSRFSGSRSGTDFTLTISSLQPEDFATYYCQQSSSSLITFGQGTKVEIKRTVAAPSVFIFPP

SDSQLKSGTASVVCLLNNFYPREAKVQWKVDNALQSGNSQESVTEQDSKDSTYSLSSTLTLSKADYEKHKVY

ACEVTHQGLSSPVTKSFNRGEC

Heavy chain:
FLLASMFVFSIATNAYAEISEVQLVESGGGLVQPGGSLRLSCAASGFNFSSSSIHWVRQAPGKGLEWVASIS

SSSGSTSYADSVKGRFTISADTSKNTAYLQMNSLRAEDTAVYYCARQYESVWNWYIGLDYWGQGTLVTVSSA

STKGPSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTSRHHHHHH

WT EcPhnD

SEQ ID NO: 11

EEQEKALNEG IISTESQQNL KPQWTPFLQD MEKKLGVKVN AFFAPDYAGI IQGMRENKVD

IAWYGNLSAM EAVDRANGQV FAQTVAADGS PGYWSVLIVN KDSPINNLND LLAEREDLIE

GNGDPNSTSG FLVPGYYVFA KNNISASDFK RTVNAGHETN ALAVANKQVD VATNNTENLD

KLKTSAPEKL KELKVIWKSP LIPGDPIVWR KNLSETTKDK IYDEFMNYGK TPEEKAVLER

LGWAPFRASS DLQLVPIRQL ALFKEMQGVK SNKGLNEQDK LAKTTEIQAQ LDDLDRLNNA

LSAMSSVSKA VQ

His Tag

SEQ ID NO: 12

GSHHHHHH

The following Examples provide illustrative embodiments of the disclosed engineered proteins, illustrative embodiments of methods to produce these engineered proteins, and illustrative embodiments of methods of detecting glyphosate with the engineered proteins.

Example 1

The crystal structure of PhnD bound to 2-AEP shows that the hydroxyls of residues Tyr47, Try93, Ser127, Thr128 and Ser129 coordinate the phosphonate moiety of 2-AEP, whereas the carboxylates of Glu177 and Asp205 bind to the amino group. Since 2-AEP and glyphosate share the same phosphonate moiety, focus was on replacing Glu177 and/or Asp205 to accommodate the longer glyphosate molecule and its carboxylic acid. Kunkel mutagenesis was used to construct a set of single or double mutants of PhnD. In some embodiments, the mutants also contained an additional cysteine mutation at position 126 for attachment of acrylodan (fluorescent reporter). In some embodiments, the mutants also contained a C-terminal histidine tag (SEQ ID NO: 12) for purification using immobilized metal affinity chromatography.

Example 2

Mutants: PND 177N (SEQ ID NO: 1), 205S (SEQ ID NO: 4), 177N 205S (SEQ ID NO: 3), and PND 177NΔ (SEQ ID NO 2) were constructed, each with a single point mutation in the binding pocket with the goal to increase the affinity for glyphosate. *E. coli* BL21 DE3 cells were used for transformation with each of the plasmid carrying the specific point mutation. To express each mutant, bacterial cultures were grown on 2×YT media with ampicillin at 37° C. at 300 rpm. IPTG was added at mid-log phase to induce expression of the proteins. Proteins obtained were purified using Immobilized Metal Affinity Chromatography (IMAC) using the AKTA Start Fast Protein Liquid Chromatography (FPLC) system and analyzed on a polyacrylamide gel. Proteins were then buffer exchanged into a low salt working buffer and their concentrations were obtained using UV spectroscopy. Proteins were then dialyzed using a semipermeable membrane to separate out all phosphate present in solution from the protein to limit background noise. PhnD undergoes a conformational change upon binding to its ligand from an open to a closed conformation. This conformational change was used to attach the fluorescent sensor Acrylodan to the protein at a specific site (126C) near the binding pocket.

Example 3

The fluorescent reporter group attached to PhnD changes its emission properties in response to glyphosate binding which can be observed using fluorescent spectroscopy. This allows detection of a ligand (in this case glyphosate), where fluorescence emission can be used to determine the concentration of glyphosate in solution. Two main types of data were collected, Apo vs Saturated spectra showing fluorescence emission with and without glyphosate (not shown), and the other type was titrations done with increasing glyphosate concentrations to determine the $K_d$ value for each mutant for glyphosate.

The purified, fluorescently-labeled mutants were tested for their ability to bind to glyphosate. $K_d$ values were determined by monitoring the changes in fluorescence as a function of increasing ligand concentrations. Table 1 provides dissociation constants ($K_d$ values) of different PhnD variants for glyphosate. All mutants contain a cysteine at position 126 for attachment of acrylodan. Values were obtained by monitoring fluorescence change as a function of ligand concentration using eq. 1.

$$R = R_0 + \frac{R_{max}}{1 + \frac{K_d}{[L]}}$$ eq. 1

TABLE 1

Dissociation constants of engineered proteins ability to bind glyphosate

| Engineered protein | SEQ ID NO | $K_d$ for glyphosate (μM) |
|---|---|---|
| Wild Type (control) | 5 | 650 |
| D205N | 4 | 600 |
| E177N, D205S | 3 | 98 |
| E177N | 1 | 8.0 |
| E177NΔ | 2 | 4.2 |

The E177N mutant (also referred to as PND177N) showed an 80-fold increase in affinity over the wild-type protein. This was achieved by mutating the glutamic acid residue at position 177 to an asparagine (E177N). The $K_d$ of the mutant for glyphosate is 8.05±0.30 μM (FIG. 1) compared to the wild type PhnD, which has a $K_d$ of ~650 μM. Based on the structure of PhnD in complex with 2-AEP, changing the glutamic acid residue to an asparagine allows for the larger glyphosate molecule to bind, while replacing a negatively charged side chain with an amide to accommodate the carboxylate of glyphosate.

Additional mutant (PND177NΔ also referred to as E177NΔ) was constructed where the C-terminal 9 amino acids were truncated. These residues have been shown to be involved in dimerization, a property that is unique to PhnD among other PBPs. The truncated mutant improved the affinity for glyphosate with a $K_d$ of 4.2 μM (as shown in Table 1), enhancing the overall binding affinity by over 150-fold.

Example 4

Figure 2:
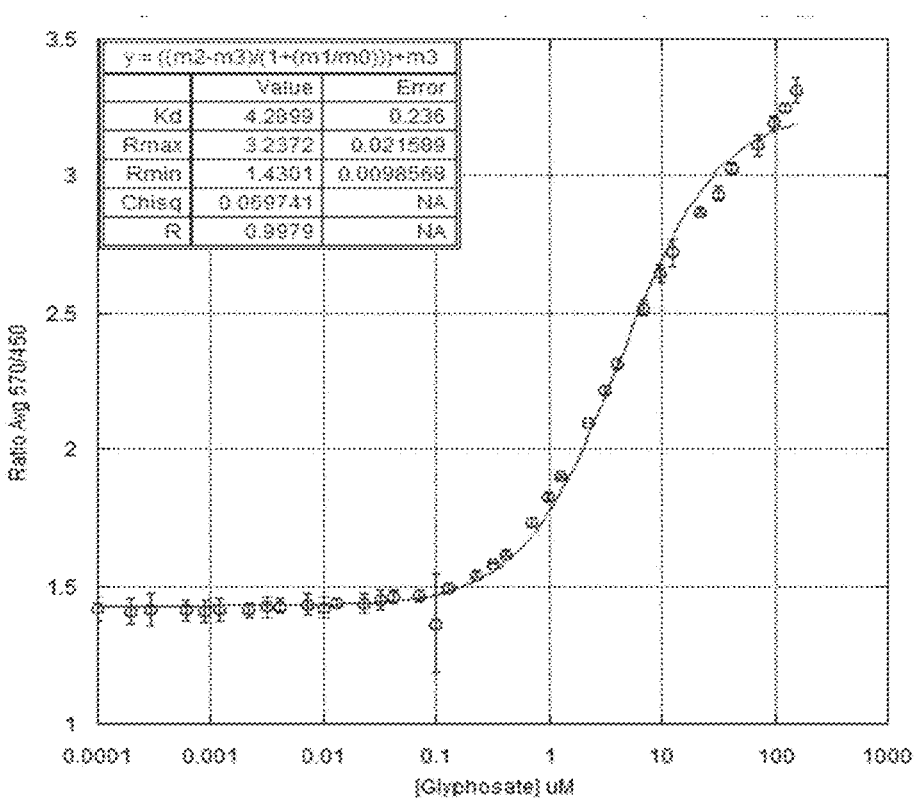
FIG. 2 shows the average titration of 177NΔ with acrylodan using glyphosate.
Figure 3:
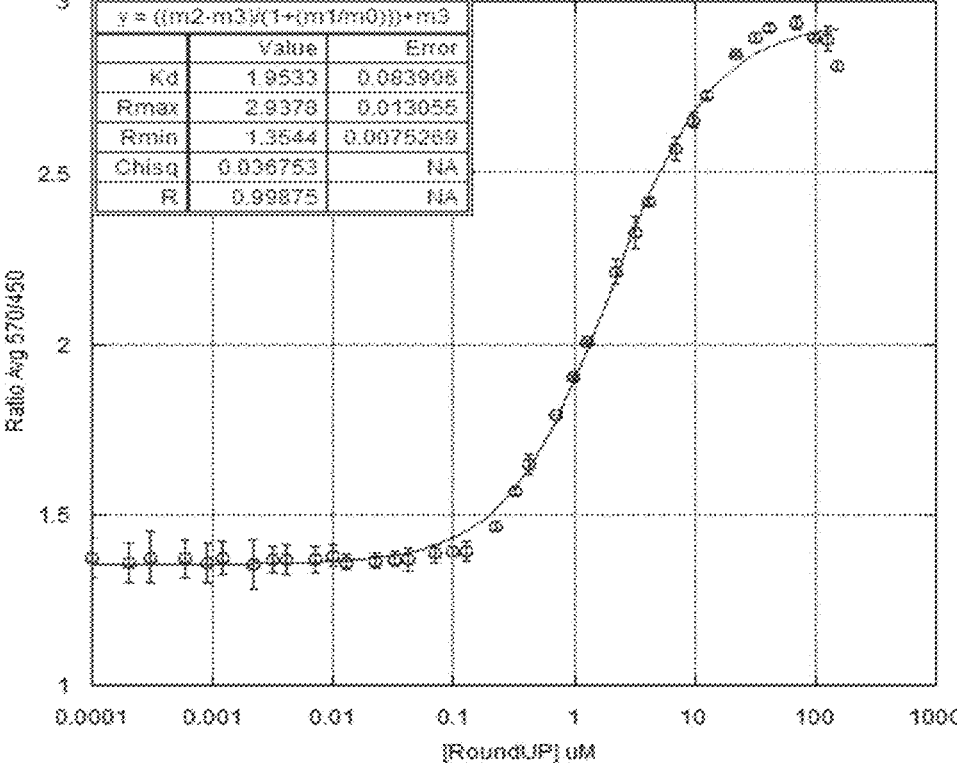
FIG. 3 shows the average titration of 177NΔ with acrylodan using ROUNDUP.
Figure 4:
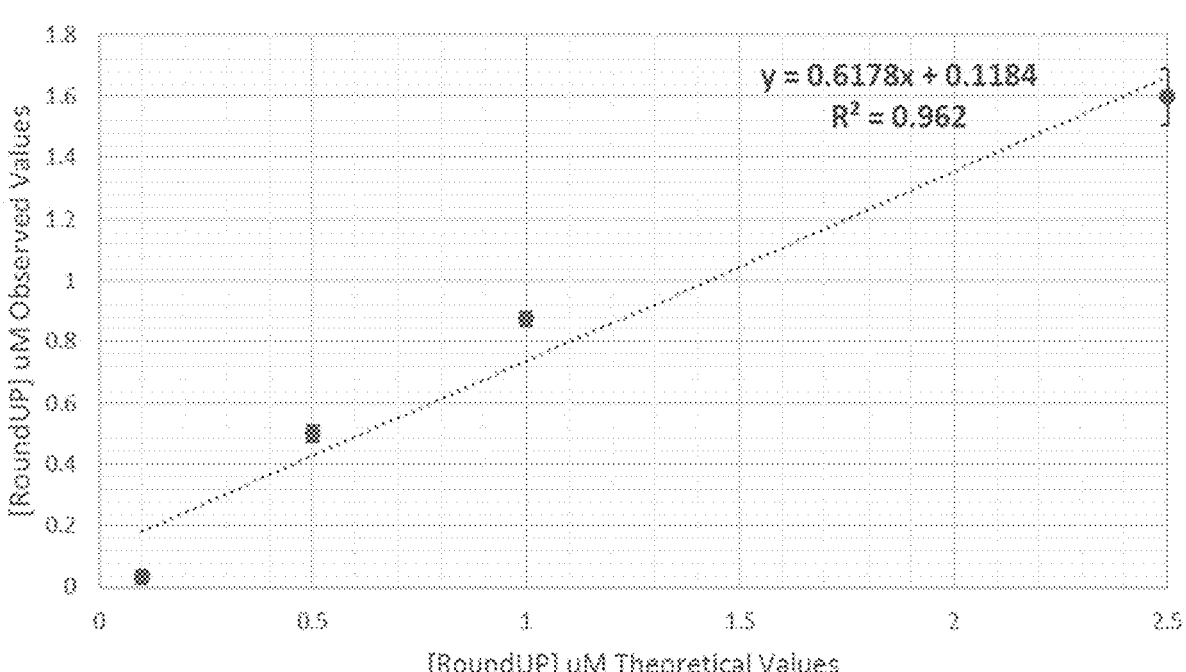
FIG. 4 shows a standard calibration curve for ROUNDUP.
Figures 5, 6:
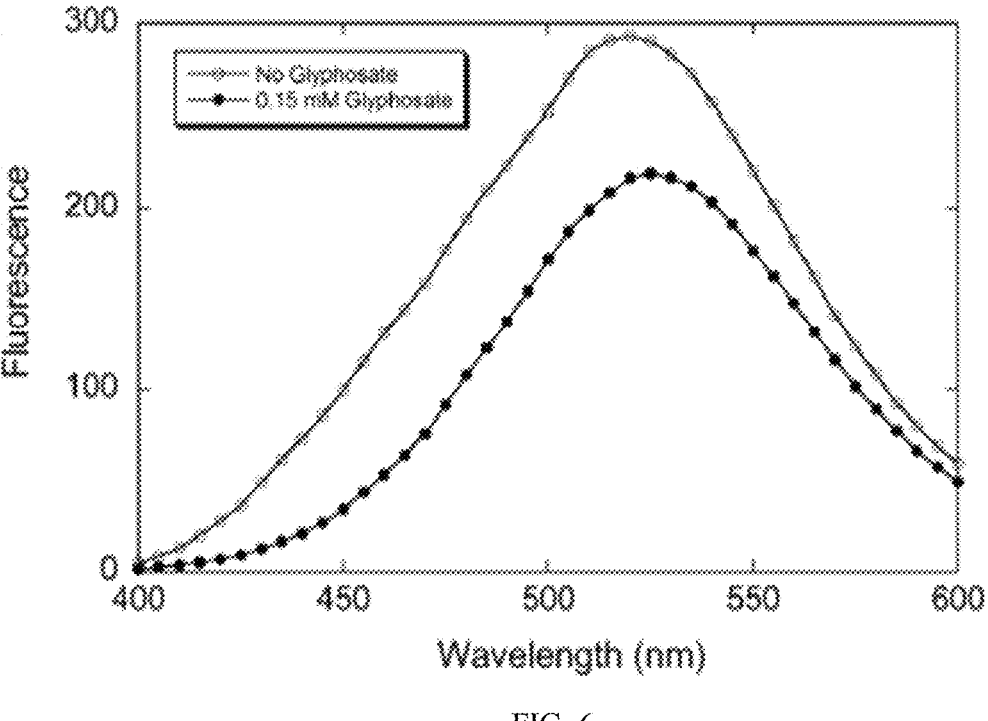
FIG. 5 shows the chemical structures of glyphosate and 2-AEP.
FIG. 6 shows change in fluorescence of the PhnD-E177NΔ-acrylodan conjugate in response to saturating concentrations of glyphosate

Spectral analysis of the fluorescence change associated with glyphosate binding to the sensor (PND177NΔ) showed a large decrease in fluorescence (FIG. 6). This decrease in the fluorescence is similar to that observed with the wild-type protein, indicating that the mutations did not severely impact the coupling of ligand binding to conformational change. Importantly, the change in fluorescence associated with ligand binding is ratiometric with a larger decrease in emission at lower wavelengths. To determine the $K_d$ values, the ratio of fluorescence between two wavelengths (570 nm/450 nm) was monitored as a function of increasing ligand concentrations (FIGS. 2 and 3). The titration data were fit to a single binding isotherm equation (eq. 1), where R is defined as the fluorescence ratio at a given ligand concentration [L], $R_0$ is the fluorescence ratio in the absence of ligand and $R_{max}$ is the fluorescence ratio at saturating ligand concentrations.

The equation was also used to determine the affinity of the sensor for commercial ROUNDUP, which contains 18.0% glyphosate isopropylamine as well as "other ingredients." In contrast with pure glyphosate acid, commercial ROUNDUP contains isopropylamine and other additives that could conceivably interfere with the ability of the sensor to detect the glyphosate content. A titration performed using diluted ROUNDUP solution in working buffer (50 mM MOPS 150 mM NaCl, pH 6.9) revealed a $K_d$ of ~2 μM (FIG. 3) indicating the ability of the sensor to detect the presence of glyphosate in the commercially available mixture.

Example 5

To examine the specificity of the sensor, we determined the affinity of the sensor for a number of compounds with similar structure to glyphosate. Table 2 shows the specificity of the PhnD-E177NΔ sensor for glyphosate, ROUNDUP and related molecules. The sensor exhibited high affinity for ROUNDUP, while the affinity for 2-AEP was greatly reduced compared to the wild-type protein by more than 3 orders of magnitude. The sensor also showed moderate affinities for phosphate and arsenate.

TABLE 2

Comparison of binding affinity between WT (SEQ ID NO: 5) and PND177Δ (SEQ ID NO: 2)

| Ligand | WT $K_d$ | PND177NΔ $K_d$ |
|---|---|---|
| Glyphosate | 650 μM | 4.29 μM |
| RoundUp | ND | 1.95 μM |
| 2-Aminoethyl Phosphate (2-AEP) | 0.002 μM | 5.61 μM |
| Phosphate | 260 μM | 26.1 μM |
| Arsenate | 230 μM | 10.7 μM |

Example 6

To test the ability of the sensor to detect the presence of glyphosate in samples contaminated with ROUNDUP, test solutions with different glyphosate concentrations were prepared by diluting ROUNDUP in working buffer. First, the initial fluorescence ratio of the sensor was recorded and used as $R_0$ (equation 1). Then, a sample of the test solution was added to the sensor and the fluorescence ratio was recorded. Saturating amounts of glyphosate were then added to the sensor following each measurement to establish the Rmax. The glyphosate concentration in each test sample was calculated using a rearrangement of equation 1. The results show a linear correlation between the theoretical concentrations of glyphosate and those determined using the sensor. Further, the sensor can detect concentrations as low as 500 nM, well below the permitted limit for drinking water in the United States.

Example 7

Antibody fragments that bind specifically to the closed (glyphosate-bound) form of EcPhnD were engineered. A phage display selection was performed by using a Fab library to select for specific antibody fragments (Fabs) that can bind to the closed form of PhnD. A fab is an antibody fragment protein that binds to a specific spot on a target protein. Fab binding can be very specific and target one conformational state of a target protein. Conformation-specific Fabs can, therefore, distinguish between the open and closed form of PhnD. According to Le Chatelier's principle, Fabs that bind specifically to the closed form of PhnD would drive the equilibrium from the open form to the closed form. By stabilizing the bound form of the protein, these Fabs would further enhance the affinity of PhnD for glyphosate. Using the phage display selection technique, we were able to generate a set of 5 Fabs: Fab N1 (SEQ ID NO: 6), Fab N2 (SEQ ID NO:7), Fab N3 (SEQ ID NO: 8), Fab N4 (SEQ ID NO: 9), and Fab N5 (SEQ ID NO: 10) that recognized closed form of PhnD. Using fluorescence spectroscopy, data showing Apo and saturated form with fab were obtained as well as titration of PhnD in the presence of Fabs to determine the Kd of the proteins for glyphosate.

By taking advantage of Le Chatelier's principle, specific Fabs were designed that stabilize the bound form of PhnD. Optimization of such enhancements is within the skill in the art. See Rizk, S. S., et al., Nat Struct Mol Biol, 2011. 18(4): p. 437-42; and Mukherjee, et al, J. Mol. Biol. 2018, 293: 2815, the contents of which are incorporated herein by reference.

Fab N2 (SEQ ID NO: 7) significantly increased binding affinity for glyphosate. Titration data (FIG. 1) showed that by adding the Fab N2, the $K_d$ (0.45±0.10 μM) improved by roughly an additional 18-fold compared to the mutant in the absence of Fab N2. This provides evidence that Fab N2 is driving protein towards the closed form, thereby enhancing glyphosate binding. However, this decreases the overall change in fluorescence reducing the signal-to-noise ratio. The combined effect of the point mutation and the Fab result in a ~1500 fold affinity enhancement, allowing the development of sensitive biosensors for environmental GP pollution.

Example 8

The observed fluorescence change in the biosensor is ratiometric. Instead of monitoring the absolute change in fluorescence intensity at a single wavelength (which is measured in arbitrary units), ratiometric analysis monitors the change in the shape of the fluorescence emission peak in response to ligand binding, providing a more deterministic relationship between the fluorescence change and ligand concentration The change in fluorescence observed with the biosensor (PhnD177NΔ, SEQ ID NO:2) resembles the overall change observed with the wild-type protein, showing that the mutations do not destroy the linkage between ligand binding and conformational change.

Figure 7:
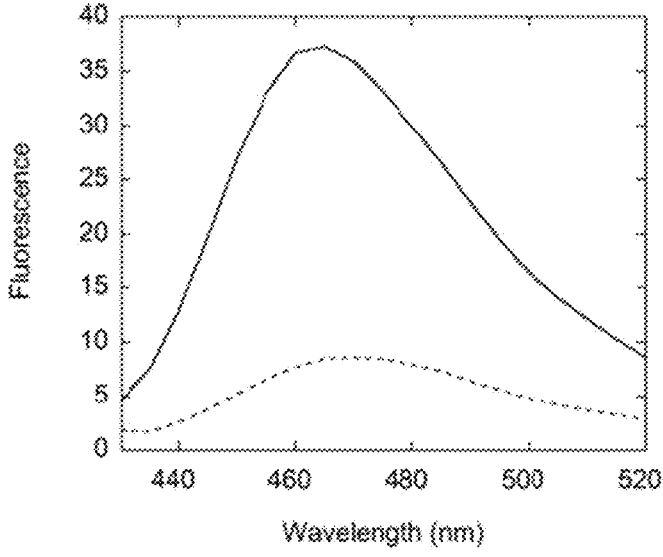
FIG. 7 shows a change in fluorescence of the glyphosate biosensor in response to ROUNDUP; wherein the solid line is the biosensor in the absence of ROUNDUP and the dashed line is the biosensor in the presence of 1 mM ROUNDUP.
Figure 8:
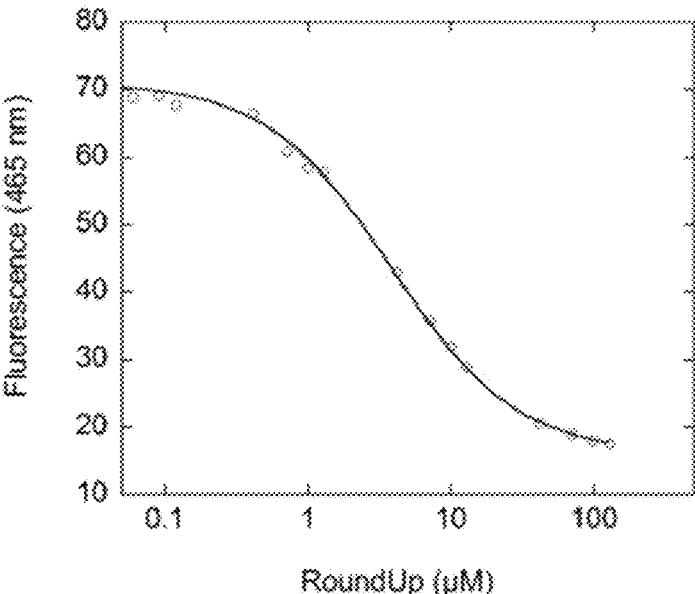
FIG. 8 shows a titration of the PND177NΔ-coumarin sensor with commercial ROUNDUP ($K_d$=4 μM).
Figure 9:
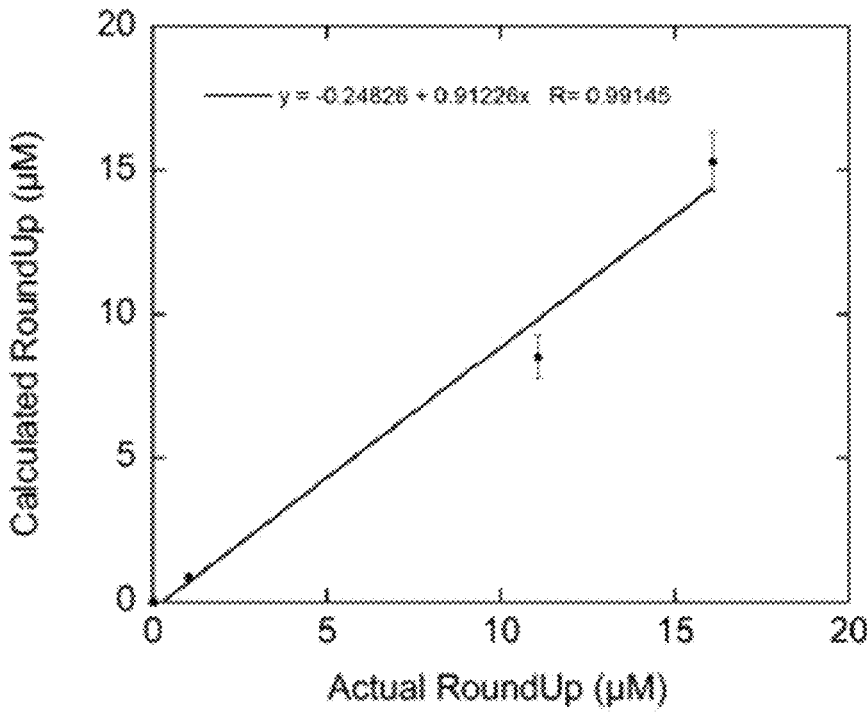
FIG. 9 shows a linear correlation between actual and calculated concentrations of glyphosate in commercial ROUNDUP using the PND177NΔ-Coumarin conjugate.

In an effort to enhance the change in fluorescence in response to ligand binding, we tested a number of thiol-reactive fluorophores. Of the fluorophores, Coumarin (7-Diethylamino-3-(4'-Maleimidylphenyl)-4-Methylcoumarin) showed a 6-fold decrease in fluorescence in response to ROUNDUP (FIG. 7) and exhibited a similar affinity to the acrylodan conjugate with a $K_d$ of 4 μM (FIG. 8). To test the ability of the sensor to detect the presence of glyphosate in samples contaminated with ROUNDUP, several test solutions with different glyphosate concentrations were prepared by diluting ROUNDUP in working buffer. Initial fluorescence was recorded, then the fluorescence value was recorded again after addition of the test solution. The fluorescence values were used to calculate the concentration of each test solution. The results show a linear correlation between the expected concentrations of glyphosate and those determined using the sensor (FIG. 9).

Figure 10:
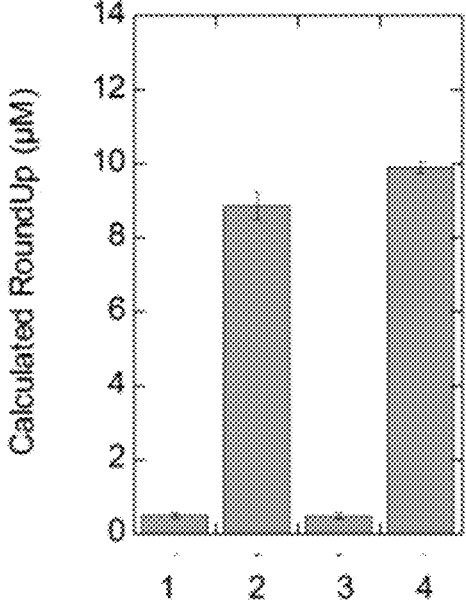
FIG. 10 shows a determination of glyphosate concentrations in soil samples treated with ROUNDUP, wherein soil samples were treated with working buffer alone (1), ROUNDUP diluted in working buffer (2), tap water alone (3), or ROUNDUP diluted with tap water (4). Actual concentrations of glyphosate in 2 and 4 are 10 μM.

Further, the biosensor can detect concentrations as low as 1 μM, well below the permitted limit for drinking water in the United States. We also used the sensor to test soil samples doped with ROUNDUP. First, ROUNDUP was diluted according to the manufacturer's recommendation (6 fl. oz. per gallon to a concentration of 37 mM) in either tap water or working buffer. Then the dilutions were added to soil samples. The samples were then centrifuged, and the supernatants were further diluted to 10 μM with working buffer and added to the PND177NΔ-Coumarin conjugate, and fluorescence values were used to obtain the concentration of glyphosate in each sample. The results show that the sensor can accurately detect ROUNDUP and determine the concentration of glyphosate in soil samples (FIG. 10).

Example 9

Sensors developed based on the PBP scaffold can be immobilized on a surface in a specific orientation and retain their ability to respond to the ligand. A similar strategy can be used with the sensor described here to monitor glyphosate concentration in real-time. This may be beneficial in water treatment facilities by monitoring pollutant concentrations in a flow-cell. Fluorescence monitoring offers the ability to use mobile hand-held devices for field monitoring without the use of bulky equipment.

Finally, the use of PBPs for developing biosensors in not limited to fluorescence detection. Different strategies link changes in conductivity with the ligand-mediated conformational change, allowing for amperometric signals to indicate ligand concentration. Other strategies rely on the attachment of a redox center to PBPs to allow for an electrochemical signal change in response to ligand binding

Example 10

Cloning and site-directed mutagenesis. The phnD gene containing the N126C mutation was cloned into a pET21a expression vector with a C-terminal 6-histidine tag (SEQ ID NO 12). Kunkel mutagenesis was used to introduce point mutation within the binding pocket of PhnD (E177N, E177N/D205S, D205N) as well as a deletion of the C-terminal six or nine amino acids responsible for dimerization (PhnDA, and PhnD177NΔ). Sequences of all mutants were confirmed by DNA sequencing at the genomics facility at the University of Chicago.

Example 11

Protein expression and purification. BL-21 DE3 chemically competent *E. coli* cells were transformed by heat shock. A single colony was used to inoculate an overnight culture of 2XYT supplemented with ampicillin. The overnight culture was used to inoculate 500 mL 2XYT medium with ampicillin, and induced at $OD_{600}$ of ~0.8-1 with 1 mM IPTG, then allowed to grow for an additional 4 hours at 37° C. with shaking at 300 rpm. Cells were harvested by centrifugation for 10 mM at 8000 rpm, resuspended in 10 mL of 20 mM Tris, 500 mM NaCl, 10 mM Imidazole pH 8.6, sonicated on ice for 6 mM with 30 second on/off intervals, then centrifuged again at 8000 rpm for 30 min to 1 hour to separate the lysate from the pellet. Proteins were purified from the lysate using Immobilized Affinity Chromatography (IMAC) on an AKTA Start system and eluted using a linear gradient from 10 mM to 300 mM imidazole. Polyacrylamide gel electrophoresis was used to verify the size of the protein, then the samples were buffer exchange into a working buffer: 50 mM MOPS, 150 mM NaCl pH 6.9 using a desalting column (Econo-Pac DG10 from Bio-Rad). Typical yield is 2-3 mg of protein per liter of culture.

Example 12

Fluorophore conjugation. The proteins were incubated with a 10-fold molar excess of fluorophore (stock concentration of 10 or 20 mM in DMSO) in the presence of 1 mM TCEP. The fluorophores tested were acrylodan (6-acryloyl-2-dimethylaminonaphthalene), IANBD (N,N'-Dimethyl-N-(Iodoacetyl)-N'-(7-Nitrobenz-2-Oxa-1,3-Diazol-4-yl)Ethylenediamine), Coumarin (7-Diethylamino-3-(4'-Maleimidylphenyl)-4-Methylcoumarin), AlexaFluor 488 C5 Maleimide, Texas Red maleimide, and tetramethyl rhodamine maleimide. Reactions were incubated overnight on an inverter, then a desalting column was used to remove excess fluorophore. The labeled proteins were dialyzed 3 times for at least 2 hours in working in 2 L of working buffer to remove any bound ligand.

Example 13

Fluorescent screening and data Analysis. All fluorescence measurements were collected on a SpectraM2 fluorescence spectrometer at 22° C. Acrylodan excitation was set-up at 359 nm and an emission sweep was collected between 400-600 nm. Coumarin conjugated PhnD was excited at 419 nm and an emission spectrum was collected between 430-520 nm. Titrations were performed by increasing concentration of ligand and monitoring the changes in fluorescence intensity at 465 nm for coumarin conjugates or the ratio of fluorescence at 570 nm/450 nm. Error bars represent the standard deviation from three individual titrations. The fluorescence intensity at each wavelength was measured three times for each ligand concentration and the average of the reading was calculated. The ratio of the two averages from each of the three titrations was used to calculate the standard deviation. $K_d$ values were determined by fitting the titration data to the following single binding isotherm equation using Kaleidagraph, where F is the observed fluorescence at a certain ligand concentration [L], $F_o$ is the fluorescence in the absence of ligand, and $F_{max}$ is the fluorescence at saturating ligand concentrations.

$$F = F_o + \frac{F_{max} - F_o}{1 + \frac{K_d}{[L]}}$$ eq. 2

To determine the concentration of glyphosate in standard solutions and soil extracts, the initial fluorescence, $F_0$, of the PND177NΔ-Coumarin conjugate was recorded, then a sample of the test solution was added to the PND177N and the fluorescence (FL) at 465 nm was recorded. Saturating amounts of glyphosate were then added to the sensor following each measurement to establish the maximum fluorescence, $F_{max}$. The obtained fluorescence values were used to calculate the concentration of ROUNDUP using the following equation:

$$[RoundUp] = \frac{Kd(F_L - F_o)}{F_{max} - F_o}$$ eq 3

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents.

---

The invention claimed is:

1. An engineered protein biosensor having an N-terminal and a C-terminal comprising:
   (i) an amino acid sequence comprising 312 amino acids and wherein the amino acid sequence is SEQ ID NO: 1; and
   (ii) a fluorescent reporter coupled to the amino acid at position 126 of the engineered protein,
   wherein amino acid at position 177 is an asparagine.

2. The engineered protein of claim 1, wherein the fluorescent reporter is selected from the group consisting of acrylodan, Coumarin (7-Diethylamino-3-(4'-Maleimidylphenyl)-4-Methylcoumarin), danzyl aziridine, 4-[N-[(2-iodoacetoxy)ethyl]-N-methylamino]-7-nitrobenz-2-oxa-1, 3-diazole ester (IANBDE), 4-[N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas Red, C5-Bromoacetamide, Alexa Fluor 750 C5-maleimide, and BODIPY 577/618.

3. The engineered protein of claim 1, wherein the fluorescent reporter is acrylodan or Coumarin (7-Diethylamino-3-(4'-Maleimidylphenyl)-4-Methylcoumarin).

4. The engineered protein of claim 1, wherein the fluorescent reporter is covalently linked to a cysteine at amino acid position 126 of the engineered protein.

5. The engineered protein of claim 1, wherein the C-terminal comprises a modification of truncating the last nine amino acids.

6. An engineered protein biosensor having an N-terminal and a C-terminal comprising:
   (i) an amino acid sequence comprising 312 amino acids and wherein the amino acid sequence is SEQ ID NO: 2; and
   (ii) a fluorescent reporter coupled to the amino acid at position 126 of the engineered protein.

7. The engineered protein of claim 6, wherein the fluorescent reporter is selected from the group consisting of acrylodan, Coumarin (7-Diethylamino-3-(4'-Maleimidylphenyl)-4-Methylcoumarin), danzyl aziridine, 4-[N-[(2-iodoacetoxy)ethyl]-N-methylamino]-7-nitrobenz-2-oxa-1, 3-diazole ester (IANBDE), 4-[N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas Red, C5-Bromoacetamide, Alexa Fluor 750 C5-maleimide, and BODIPY 577/618.

8. The engineered protein of claim 6, wherein the fluorescent reporter is acrylodan or Coumarin (7-Diethylamino-3-(4'-Maleimidylphenyl)-4-Methylcoumarin).

9. The engineered protein of claim 6, wherein the fluorescent reporter is covalently linked to a cysteine at amino acid position 126 of the engineered protein.

10. The engineered protein of claim 6, wherein the C-terminal comprises a modification of truncating the last nine amino acids.

* * * * *